United States Patent [19]

Widmer

[11] Patent Number: 5,082,842
[45] Date of Patent: Jan. 21, 1992

[54] TRICYCLIC PYRIDONE DERIVATIVES

[75] Inventor: Ulrich Widmer, Rheinfelden, Switzerland

[73] Assignee: Hoffmann-La Roche Inc., Nutley, N.J.

[21] Appl. No.: 422,197

[22] Filed: Oct. 16, 1989

Related U.S. Application Data

[62] Division of Ser. No. 198,539, May 25, 1988, Pat. No. 4,889,854.

[30] Foreign Application Priority Data

Jun. 12, 1987 [CH]  Switzerland ............... 2206/87
Apr. 8, 1988 [CH]  Switzerland ............... 1297/88

[51] Int. Cl.$^5$ ............................. A61K 31/395
[52] U.S. Cl. .................. 514/248; 514/228.5; 514/233.2; 544/60; 544/66; 544/115; 544/234
[58] Field of Search ............ 544/234, 60, 66, 115; 514/248, 228.5, 233.2

[56] References Cited

U.S. PATENT DOCUMENTS

| | | | |
|---|---|---|---|
| 4,236,010 | 11/1980 | Imhof et al. | 546/138 |
| 4,735,940 | 4/1988 | Fischer et al. | 514/212 |
| 4,855,297 | 8/1989 | Fischer et al. | 544/234 |

FOREIGN PATENT DOCUMENTS 0157346 10/1985 European Pat. Off.

OTHER PUBLICATIONS

Monatsh. Chem. 98, 2148–2156 (1967), Kappe et al.
Monatsh. Chem. 100, 1726–1734 (1969), Kappe et al.
Chem. Pharm. Bull 22(4), 744–751 (1974), Kato et al.
Chem. Pharm. Bull. 21(5) 921–925 (1973), Kobayashi et al.
J. Heterocyclic Chem. 18, 1451–1456 (1981), Torrini et al.
Chemical Abstract 87, 84933n (1977), Talukdar et al.
Chemical Abstract 89, 107293n (1978), Talukdar et al.
Chemical Abstracts 89, 197,445r (1978), Singh et al.
Chemical Abstracts 92 215,321r (1980), Singh et al.
Pharmazie 23, 301–303 (1968), Buchmann et al.
Can. J. Chem. 63, 882–886 (1985), McKinnon et al.
J. Org. Chem. 50, 1666–1676 (1985), Potts et al.
J. Org. Chem. 50, 1677–1681 (1985), Potts et al.
J. Org. Chem. 37(11), 1823–1825 (1972), Goldberg et al.

*Primary Examiner*—Mary C. Lee
*Assistant Examiner*—Jacqueline Haley
*Attorney, Agent, or Firm*—George M. Gould; William G. Isgro; Ellen Ciambrone Coletti

[57] ABSTRACT

The compounds of the formula

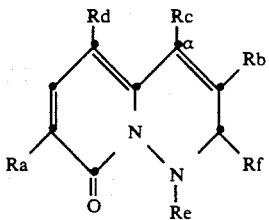

A wherein Ra, Rb, Rc, Rd, Re and Rf are defined in the specification, and the pharmaceutically acceptable acid addition salts of compounds of formula A which have one or more basic substituents are described. The compounds of formula A have valuable pharmacological properties and can be used for the control or prevention of illnesses. In particular, they have muscle relaxant, sedative-hypnotic, anxiolytic and/or anticonvulsive activity and can accordingly be used in the control or prevention of muscle tensions, stress conditions, insomnia, anxiety states and/or convulsions.

28 Claims, No Drawings

TRICYCLIC PYRIDONE DERIVATIVES

This is a division of application Ser. No. 07/198,535 filed May 25, 1988, now U.S. Pat. No. 4,889,854.

BRIEF DESCRIPTION OF THE INVENTION

The invention relates to tricyclic pyridone derivatives of the formula

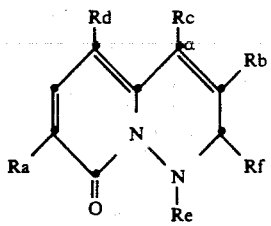

A wherein Ra is phenyl, pyridyl or thienyl group which is optionally substituted by halogen, trifluoromethyl, nitro, lower alkyl or lower alkoxy, Rb and Rc together with the carbon atom denoted by $\alpha$ are a group of the formula $>C_\alpha-S-CH=CH-$ (a), $>C_\alpha-CH=CH-S-$ (b) or $>C_\alpha-CH=CH-CH=CH-$ (c) which is optionally substituted by halogen, trifluoromethyl, lower alkyl, lower alkoxy, nitro, amino or mono- or di(lower alkyl)amino, Rd is the group of the formula $-(A^1)_m-(CO)_n-(Q^1A^2)_q-R^1$, m, n and q each are the number 0 or 1, $A^1$ is lower alkylene. $A^2$ is lower alkylene, a direct bond or the group $-CO-$, $Q^1$ is an oxygen atom or the group $-NR^2-$, $R^1$ is hydrogen, hydroxy, cyano, nitro, halogen, lower alkoxy, lower alkyl, lower alkoxycarbonyl, aryl, a group of the formula $-NR^3R^4$ or a 5-membered saturated, partially unsaturated or aromatic heterocycle which is attached via a carbon atom and which is optionally substituted by one or two lower alkyl groups and optionally substituted by a $(C_{3-6})$-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)-carbamoyl, oxo or alkylenedioxy group, $R^2$ is hydrogen, lower alkyl or aryl, $R^3$ and $R^4$ each, independently, is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$-cycloalkyl group which is optionally substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or $R^3$ and $R^4$ together with the nitrogen atom are a 3- to 7-membered saturated N-heterocycle which is optionally substituted by one or two lower alkyl groups and optionally substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group $>N-R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, Re is hydrogen, lower alkyl, lower alkanoyl, arylcarbonyl, aryl-(lower alkanoyl), aryl-(lower alkyl) or lower alkenyl and Rf is hydrogen or lower alkyl, with the proviso that n is the number 0 when q is the number 1 and $A^2$ is the group $-CO-$, that $R^1$ has a significance different from cyano, nitro, halogen or lower alkoxycarbonyl when q is the number 0 and n is the number 1 or when q is the number 1 and $A^2$ is the group $-CO-$, and that $R^1$ has a significance different from hydroxy, cyano, nitro, halogen, lower alkoxycarbonyl, lower alkoxy and $-NR^3R^4$ when q is the number 1 and $A^2$ is a direct bond, or a pharmaceutically acceptable acid addition salt of a compound of formula A which has one or more basic substituents.

DETAILED DESCRIPTION OF THE INVENTION

The invention is concerned with compounds of the formula

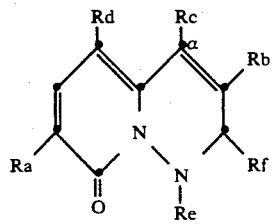

A wherein Ra is phenyl, pyridyl or thienyl group which is optionally substituted by halogen, trifluoromethyl, nitro, lower alkyl or lower alkoxy, Rb and Rc together with the carbon atom denoted by $\alpha$ are a group of the formula $>C_\alpha-S-CH=CH-$ (a), $>C_\alpha-CH=CH-S-$ (b) or $>C_\alpha-CH=CH-CH=CH-$ (c) which is optionally substituted by halogen, trifluoromethyl, lower alkyl, lower alkoxy, nitro, amino or mono- or di(lower alkyl)amino, Rd is the group of the formula $-(A^1)_m-(CO)_n-(Q^1A^2)_q-R^1$, m, n and q each are the number 0 or 1, $A^1$ is lower alkylene, $A^2$ is lower alkylene, a direct bond or the group $-CO-$, $Q^1$ is an oxygen atom or the group $-NR^2-$, $R^1$ is hydrogen, hydroxy, cyano, nitro, halogen, lower alkoxy, lower alkyl, lower alkoxycarbonyl, aryl, a group of the formula $-NR^3R^4$ or a 5-membered saturated, partially unsaturated or aromatic heterocycle which is attached via a carbon atom and which is optionally substituted by one or two lower alkyl groups and optionally substituted by a $(C_{3-6})$-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^2$ is hydrogen, lower alkyl or aryl, $R^3$ and $R^4$ each, independently, is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$-cycloalkyl group which is optionally substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)carbamoyl or by lower alkylenedioxy or $R^3$ and $R^4$ together with the nitrogen atom are a 3- to 7-membered saturated N-heterocycle which is optionally substituted by one or two lower alkyl groups and optionally substituted by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups and which can contain as a ring member an oxygen or sulfur atom or the group $>N-R^5$, and $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, Re is hydrogen, lower alkyl, lower alkanoyl, arylcarbonyl, aryl-(lower alkanoyl), aryl-(lower alkyl) or lower alkenyl and Rf is hydrogen or lower alkyl, with the proviso that n is the number 0 when q is the number 1 and $A^2$ is the group —CO—, that $R^1$ has a significance different from cyano, nitro, halogen or lower alkoxycarbonyl when q is the number 0 and n is the number 1 or when q is the number 1 and $A^2$ is the group —CO—, and that $R^1$ has a significance different from hydroxy, cyano, nitro, halogen, lower alkoxycarbonyl, lower alkoxy and —$NR^3R^4$ when q is the number 1 and $A^2$ is a direct bond, is a pharmaceutically acceptable acid addition salt of a compound of formula A which has one or more basic substituents.

The tricyclic pyridone derivatives have valuable pharmacological properties and can be used for the control or prevention of illnesses. In particular, they have muscle relaxant, sedative-hypnotic, anxiolytic and/or anticonvulsive activity and can accordingly be used in the control or prevention of muscle tensions, stress conditions, insomnia, anxiety states and/or convulsions.

Objects of the invention are: The above compounds of formula A and the aforementioned salts thereof per se; a process for their manufacture; the above compounds of formula A and the aforementioned salts thereof for use as therapeutically active substances; medicaments based on these novel active substances and their manufacture; the use of these active substances in the control or prevention of illnesses; as well as their use for the manufacture of medicaments having muscle relaxant, sedative-hypnotic, anxiolytic and/or anti-convulsive activity.

The term "lower" denotes residues and compounds having a maximum of seven, preferably a maximum of four, carbon atoms. The term "alkyl", taken alone or in combinations such as alkanoyl, alkanoyloxy and alkoxyalkyl, denotes straight-chain or branched, saturated hydrocarbon residues such as methyl, ethyl, propyl, isopropyl and t-butyl. The term "cycloalkyl" denotes cyclic, saturated hydrocarbon residues such as cyclopropyl and cyclohexyl. The term "alkoxy" denotes alkyl groups attached via an oxygen atom, such as methoxy and ethoxy. The term "hydroxyalkyl" denotes alkyl groups substituted by hydroxy, such as hydroxymethyl and 2-hydroxyethyl. The terms "alkanoyl" and "alkanoyloxy" denote fatty acid residues such as acetyl and acetoxy. The term "alkylene" denotes straight chain or branched, saturated hydrocarbon residues having two free valencies, such as methylene, 1,2-ethylene and 1,3-propylene. The term "halogen" denotes the four forms fluorine, chlorine, bromine and iodine.

The term "aryl" preferably denotes phenyl groups which are optionally substituted by halogen, trifluoromethyl, lower alkyl, lower alkoxy, nitro, amino or mono- or di(lower alkyl)amino.

The 5-membered, saturated, partially unsaturated or aromatic heterocycles which are attached via a carbon atom preferably contain as the hetero ring member(s) an oxygen or sulfur atom or an imino or lower alkylimino group and optionally one or two nitrogen atoms, with the carbon atom via which the heterocycle is attached being preferably situated adjacent to one hetero atom or between two hetero atoms. Examples of such heterocycles, which can be substituted as mentioned, are: 2-oxazolin-2-yl, 3-methyl-1,2,4-oxadiazol-5-yl, 3-cyclopropyl-1,2,4-oxadiazol-5-yl, 2-thiazolin-2-yl, 2-tetrahydrofuryl and 2-thiazolyl.

The term "3- to 7-membered, saturated N-heterocycle which can contain as a ring member an oxygen or sulfur atom or the group $>N-R^5$" as a possible value for —$NR^3R^4$ denotes on the one hand heterocycles having only one hetero atom, namely the nitrogen atom via which they are attached, and on the other hand heterocycles having two hetero atoms, namely the aforementioned nitrogen atom and an oxygen or sulfur atom or a second nitrogen atom.

Examples of such heterocycles, which can be further substituted as mentioned, are: 2-(lower alkoxyalkyl)-1-azetidinyl, 3-(lower alkoxy)-1-azetidinyl, 3-hydroxy-1-azetidinyl, 2-(lower hydroxyalkyl)-1-azetidinyl, 2-(lower alkanoyloxyalkyl)-1-pyrrolidinyl, 3-oxo-1-pyrrolidinyl, 2-(lower alkoxycarbonyl)-1-pyrrolidinyl, 3-(lower alkoxy)-1-pyrrolidinyl, 3-hydroxy-1-pyrrolidinyl, 2-(lower alkoxyalkyl)-1-pyrrolidinyl, 2-(lower hydroxyalkyl)-1-pyrrolidinyl, 2-(lower hydroxyalkyl)-4-hydroxy-1-pyrrolidinyl, 2-(lower alkoxyalkyl)-4-(lower alkoxy)-1-pyrrolidinyl, 4-morpholinyl, 2,6-di(lower alkyl)-4-morpholinyl, 4-thiomorpholinyl, 1-piperazinyl, 1-(lower alkyl)-4-piperazinyl, 1-(lower alkoxyalkyl)-4-piperazinyl, 1-(lower alkanoyl)-4-piperazinyl, 4-(lower hydroxyalkyl)-1-piperidinyl, 4-oxo-1-piperidinyl, 4-(lower alkoxy)-1-piperidinyl, 4-(lower alkoxycarbonyl)-1-piperidinyl, 4-hydroxy-1-piperidinyl, 4-(lower alkylcarbamoyl)-1-piperidinyl, 4-(lower alkanoyloxy)-1-piperidinyl, 2-(lower alkoxyalkyl)-1-piperidinyl, 2(lower hydroxyalkyl)-1-piperidinyl, 3-(lower alkoxy)-1-piperidinyl, 4,4-(lower alkylenedioxy)-1-piperidinyl and 3-hydroxy-1-piperidinyl.

The symbol Ra preferably is a phenyl group optionally substituted by m-halogen or m-trifluoromethyl, with phenyl being especially preferred.

The symbols Rb and Rc together with the carbon atom denoted by $\alpha$ preferably are a group of the formula $>C_\alpha-S-CH=CH-$ (a) or $>C_\alpha-CH=CH-CH=CH-$ (c), which is optionally substituted by halogen, especially the group of the formula $>C_\alpha-S-CH=CH-$ or $>C_\alpha-CH=CCl-CH=CH-$.

In a preferred embodiment Rd is the group —$CONR^3R^4$, $R^3$ is lower alkyl or lower alkoxy-alkyl and $R^4$ is hydrogen or lower alkyl or $R^3$ and $R^4$ together with the nitrogen atom are a 4-, 5- or 6-membered, saturated N-heterocycle which is optionally substituted by one or two lower alkyl groups or optionally substituted by a hydroxy, lower alkoxy, lower hydroxyalkyl or lower alkoxyalkyl group and which can contain an oxygen atom as a ring member.

In an especially preferred embodiment $R^3$ is lower alkyl or lower alkoxyalkyl and $R^4$ is hydrogen or lower alkyl or $R^3$ and $R^4$ together with the nitrogen atom are a 1-azetidinyl, 1-pyrrolidinyl, 1-piperidinyl or 4-morpholinyl group which is optionally substituted by one or two lower alkyl groups or optionally substituted by a hydroxy, lower alkoxy, lower hydroxyalkyl or lower alkoxyalkyl group.

In a particularly preferred embodiment $R^3$ is lower alkyl or 2-(lower alkoxy)ethyl and $R^4$ is hydrogen or lower alkyl or $R^3$ and $R^4$ together with the nitrogen atom are 3-(lower alkoxy)-1-azetidinyl, 3-(lower alkoxy)-1-pyrrolidinyl, 2-(lower alkoxyalkyl)-1-pyrrolidinyl or 4-morpholinyl.

Re preferably is hydrogen or lower alkyl, especially hydrogen or methyl. Rf preferably is hydrogen or methyl, especially hydrogen.

The compounds listed hereinafter are especially preferred representatives of the class of substance defined by formula A:

4-[(10-Chloro-6,7-dihydro-4-oxo-3-phenyl-4H-pyrido[2,1-a]phthalazin-1-yl)carbonyl]morpholine and (R)-1-[(10-chloro-6,7-dihydro-4-oxo-3-phenyl-4H-pyrido[2,1-a]phthalazin-1-yl)carbonyl]-2-(methoxymethyl)pyrrolidine.

Further preferred representatives of the class of substances in accordance with the invention are:

1-[(10-Chloro-6,7-dihydro-4-oxo-3-phenyl-4H-pyrido[2,1-a]phthalazin-1-yl)carbonyl]-3-methoxyazetidine, 10-chloro-6,7-dihydro-N,N-dimethyl-4-oxo-3-phenyl-4H-pyrido[2,1-a]phthalazine-1-carboxamide, (R)-1-[(4,5-dihydro-7-oxo-8-phenyl-7H-pyrido[1,2-b]-thieno[2,3-d]pyridazin-10-yl)carbonyl]-3-methoxypyrrolidine, 1-[(4,5-dihydro-4-methyl-7-oxo-8-phenyl-7H-pyrido[1,2-b]thieno[2,3-d]pyridazin-10-yl)carbonyl]-3-methoxyazetidine, 1-[(4,5-dihydro-5-methyl-7-oxo-8-phenyl-7H-pyrido[1,2-b]thieno[2,3-d]pyridazin-10-yl)carbonyl]-3-methoxyazetidine and 4,5-dihydro-N,N-dimethyl-7-oxo-8-phenyl-7H-pyrido[1,2-b]thieno[2,3-d]pyridazine-10-carboxamide.

The compounds of formula A and the pharmaceutically acceptable acid addition salts of those having a basic substituent can be prepared in accordance with the invention by i) reducing a compound of the formula

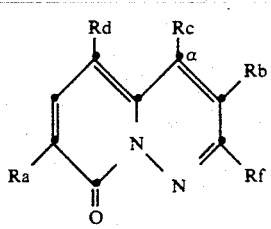

I wherein Ra, Rb, Rc, Rd and Rf have the above significance, with an alkali metal borohydride or a derivative thereof, optionally in the presence of formic acid, or ii) alkylating or acylating a compound of the formula

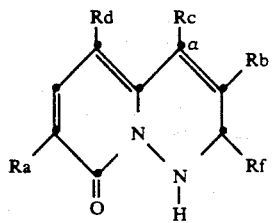

Aa wherein Ra, Rb, Rc, Rd and Rf have the above significance, with a compound of the formula Re'—X    B wherein X is a leaving group and Re' is lower alkyl, lower alkanoyl, arylcarbonyl, aryl-lower alkanoyl, aryl-lower alkyl or lower alkenyl, iii) reacting a compound of the formula

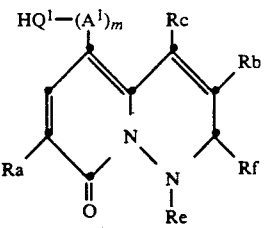

Ab wherein $A^1$, $Q^1$, m, Ra, Rb, Rc, Re and Rf have the above significance, with a reactive derivative of a carboxylic acid of the formula $R^1$—COOH    XIII wherein $R^1$ has the above significance, in the presence of an optionally strong base, and iv) if desired, converting a compound of formula A obtained which has a basic substituent into a pharmaceutically acceptable acid addition salt.

The above processes can be carried out according to methods which are known and which are familiar to any person skilled in the art.

In accordance with process variant i) there can be prepared compounds of formula A in which Re is hydrogen or, where the reaction is carried out in the presence of formic acid, methyl. Sodium cyanoborohydride under acidic conditions or lithium borohydride is preferably used as the reducing agent. Suitable solvents for the reduction with sodium cyanoborohydride are, for example, alcoholic hydrochloric acid such methanolic hydrochloric acid, acetic acid and formic acid and mixtures thereof with lower alcohols such as methanol and ethers such as tetrahydrofuran. Ethers such as tetrahydrofuran are preferably used as the solvent for the reduction with lithium borohydride. The reaction is preferably carried out at room temperature.

Compounds of formula A in which Re is lower alkyl, lower alkanoyl, arylcarbonyl, aryl-lower alkanoyl, aryl-lower alkyl or lower alkenyl can be prepared in accordance with process variant ii). In the case of alkylations the leaving group X is preferably a halogen atom, for example, a chlorine, bromine or iodine atom, and in the case of acylations the leaving group X is preferably a halogen atom, for example, a chlorine atom, or the group Re'—COO—. Suitable solvents are: halogenated lower hydrocarbons such as methylene chloride and chloroform, open-chain or cyclic ethers such as diethyl ether and tetrahydrofuran, lower fatty acid esters such as ethyl acetate, lower alcohols such as methanol, acetone, dimethylformamide and dimethyl sulfoxide. In the case of acylations with liquid anhydrides, the anhydride can also function as the solvent. The reaction is preferably carried out in a range of from room temperature to the boiling temperature of the reaction mixture.

Compounds of formula A in which Rd is a group of the formula —$(A^1)_m$—$Q^1$—CO—$R^1$ and $A^1$, $Q^1$, $R^1$ and m have the above significance can be prepared in accordance with process variant iii).

The reaction of a compound of formula Ab with a reactive derivative of a carboxylic acid of formula XIII, for example a carboxylic acid chloride, is conveniently carried out in an inert organic solvent in the presence of a base. Where Re is hydrogen and $Q^1$ is an oxygen atom, a strong base such as sodium hydride is conveniently used.

Compounds of formula A which have one or more basic substituents can be converted into pharmaceutically acceptable acid addition salts in accordance with process variant iv). There come into consideration not only salts with inorganic acids, but also salts with organic acids, for example, hydrochlorides, hydrobromides, sulfates, nitrates, citrates, acetates, maleates, succinates, methanesulfonates, p-toluenesulfonates and the like.

The compounds of formula I which are used as starting materials can be prepared by a) reacting a compound of the formula

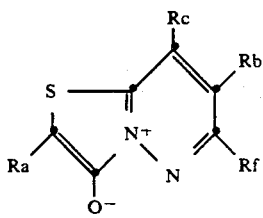  II wherein Ra, Rb, Rc and Rf have the above significance, at an elevated temperature with a compound of the formula

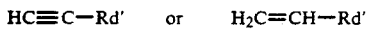

III    IV wherein Rd' is cyano, nitro or the group of the formula $-CO-(Q^1A^2)_q-R^1$ and q, $A^2$, $Q^1$ and $R^1$ have the above significance, or with phenylvinyl sulfoxide and, if necessary, treating the cycloaddition product obtained with a strong base, or b) reacting a compound of the formula

  V $ROOC-C(Ra)=CHR'$ wherein R is lower alkyl and R' is hydrogen or lower alkyl, and Ra has the above significance, at an elevated temperature when R' is hydrogen or in the presence of a strong base when R' is lower alkoxy with a compound of the formula

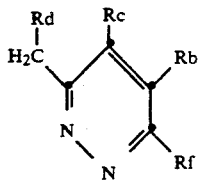  VI wherein Rb, Rc, Rd and Rf have the above significance, and dehydrogenating the cyclocondensation product obtained when R' is hydrogen, or c) hydrolzing a compound of formula I which contains an esterified carboxy group, or d) esterifying a carboxylic acid of the formula

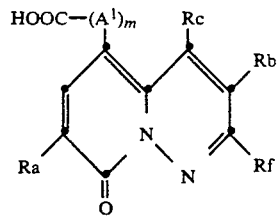  Ia wherein $A^1$, Ra, Rb, Rc, m and Rf have the above significance, with an alcohol of the formula

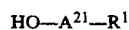  VII $HO-A^{21}-R^1$ wherein $A^{21}$ is lower alkylene or a direct bond and $R^1$ has the above significance, or e) converting a carboxylic acid of formula Ia above or a carboxylic acid of the formula

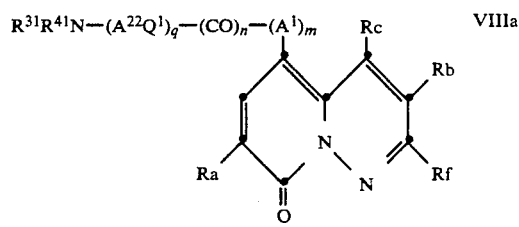  VIIIa wherein $A^{22}$ is lower alkylene or the group $-CO-$ and $R^{31}$ and $R^{41}$ together with the nitrogen atom are a 3- to 7-membered saturated N-heterocycle which is optionally substituted by one or two lower alkyl groups and which is substituted by a carboxy group and which can contain as a ring member an oxygen or sulfur atom or the group $>N-R^5$, and $A^1$, $Q^1$, Ra, Rb, Rc, $R^5$, m, n, q and Rf have the above significance, or a reactive derivative thereof into the corresponding amide with, respectively, an amine of the formula

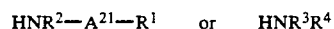

$HNR^2-A^{21}-R^1$    or    $HNR^3R^4$

IX    X wherein $A^{21}$, $R^1$, $R^2$, $R^3$ and $R^4$ have the above significance, or with ammonia or a mono or di(lower alkyl)amine, or f) reacting a compound of the formula

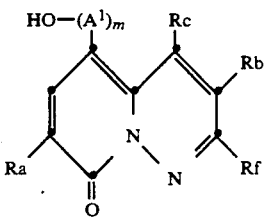  Ib wherein $A^1$, Ra, Rb, Rc, m and Rf have the above significance, in the presence of a base with a compound of the formula $X-A^{21}-R^1$    XI wherein X is a leaving group and $R^{21}$ and $R^1$ have the above significance, or reacting a compound of formula I which contains a free hydroxy group with a compound of the formula

R—X             XII wherein R is lower alkyl and X has the above significance, or g) reacting a compound of the formula

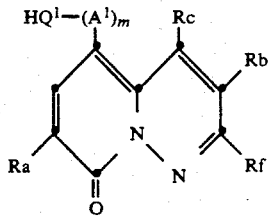                Ib wherein $A^1$, $Q^1$, Ra, Rb, Rc, m and Rf have the above significance, in the presence of an acid-binding agent with a reactive derivative of a carboxylic acid of the formula $R^1$—COOH      XIII wherein $R^1$ has the above significance, or h) reacting a compound of the formula

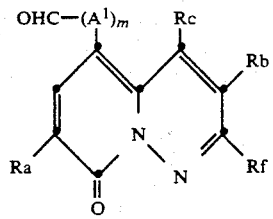                Ic wherein $A^1$, Ra, Rb, Rc, m and Rf have the above significance, in the presence of a reducing agent with an amine of formula IX or X above, or i) reducing a compound of the formula

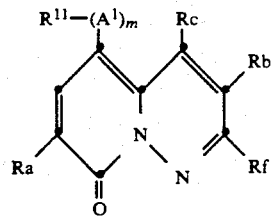                Id wherein $R^{11}$ is nitro, cyano or lower alkoxy carbonyl and $A^1$, Ra, Rb, Rc, m and Rf have the above significance, or a compound of formula Ia above or a reactive derivative thereof, or j) oxidizing an alcohol of formula Ib' above or an alcohol of the formula

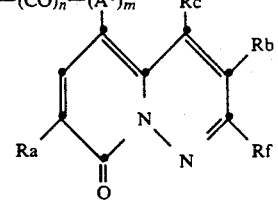             Ie wherein $A^1$, $A^2$, $Q^1$, Ra, Rb, Rc, m, n, q and Rf have the above significance, and $R^{32}$ and $R^{42}$ together with the nitrogen atom are a 3- to 7-membered, saturated N-heterocycle which is optionally substituted by one or two lower alkyl groups and which is substituted by a hydroxy group and which can contain as a ring member an oxygen or sulfur atom or the group $>N—R^5$, and $R^5$ has the above significance, k) reacting an isocyanate of the formula

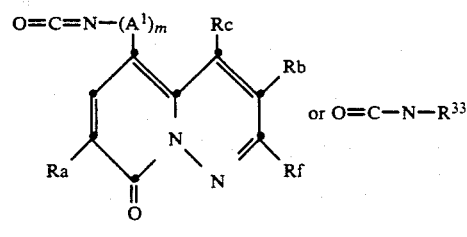

VIIIb                XIV wherein $A^1$, Ra, Rb, Rc, m and Rf have the above significance and $R^{33}$ is hydrogen, lower alkyl or $(C_{3-7})$-cycloalkyl, with, respectively, a lower alcohol or an amine of formula X above or with a compound of formula Ib above, or l) reacting a compound of the formula

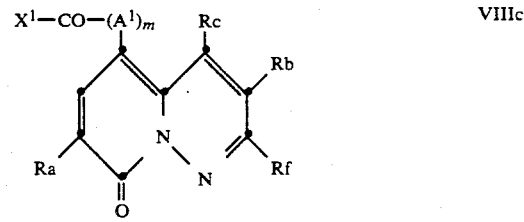            VIIIc wherein $X^1$ is a halogen atom and $A^1$, Ra, Rb, Rc, m and Rf have the above significance, with a lower alkylmagnesium halide, or m) halogenating a compound of the formula

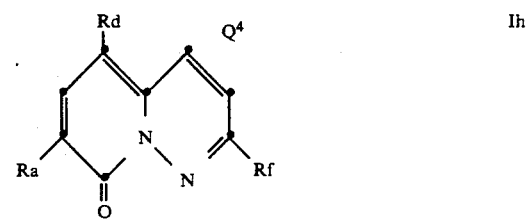           Ih wherein $Q^4$ is the group (a) or (b) above and Ra, Rd and Rf have the above significance, on the thiophene ring, or n) reacting a compound of formula VIIIc above in the presence of a base with a compound of the formula

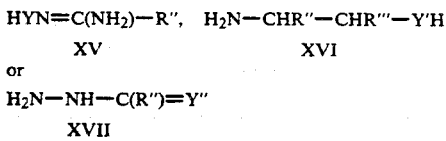

wherein Y is an oxygen atom or the group —NR'''—, Y' is an oxygen atom or the group —NH—, Y'' is an oxygen or sulfur atom and R'' and R''' each are hydrogen or lower alkyl, and cyclizing the product obtained, or o) reacting a compound of the formula

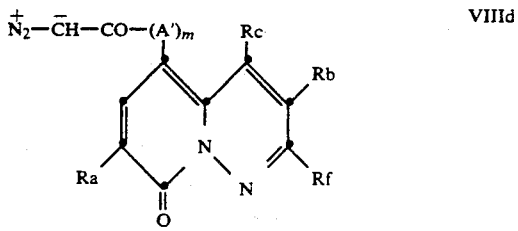

wherein A' is $C_{1-6}$-alkylene and Ra, Rb, Rc, Rf and m have the above significance, with a lower alcohol, or p) decarboxylating a carboxylic acid of formula Ia in which m is the number O, or q) halogenating a compound of formula I in which Rd is hydrogen on the pyridone ring, or r) cleaving the acetal group in a compound of the formula

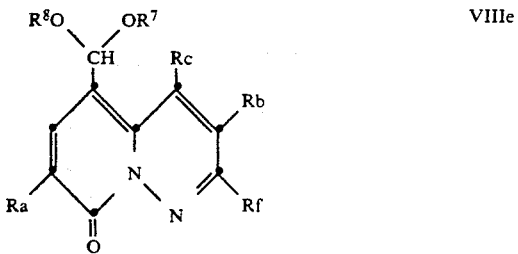

wherein $R^7$ and $R^8$ each are lower alkyl or together are lower alkylene and Ra, Rb, Rc and Rf have the above significance, or s) reacting a compound of the formula

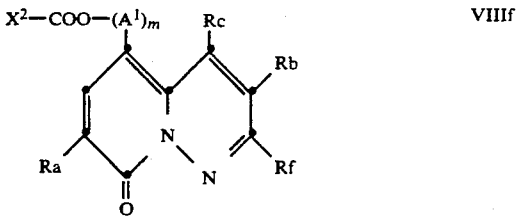

wherein $X^2$ is phenoxy and $A^1$, Ra, Rb, Rc, Rf and m have the above significance, with an amine of formula X above.

In several of the above processes the reactive amino, carboxy and/or hydroxyl groups which may be present in the starting materials must be blocked by protecting groups. These instances are readily recognizable by a person skilled in the art, and the choice of protecting groups which are suitable in a given case also presents no difficulties.

A compound of formula I in which Rd is hydrogen, cyano, nitro or the group of the formula —CO—(Q-$^1A^2$)q—$R^1$ and q, $A^2$, $Q^1$ and $R^1$ have the above significance can be prepared in accordance with process variant a). The reaction is conveniently effected in an inert solvent which boils at an elevated temperature, preferably above 80° C. Suitable solvents are, for example, aromatic hydrocarbons such as benzene, toluene and xylene, in which case the reaction is preferably carried out at the reflux temperature of the solvent.

When the reaction of a compound of formula II with a compound of formula III or with phenylvinyl sulfoxide is carried out at an elevated temperature, the corresponding compound of formula I is obtained directly. When a compound of formula II is reacted with a compound of formula IV, there is firstly obtained as the cycloaddition product the corresponding epithio compound of the formula

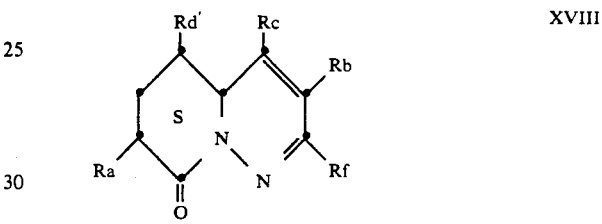

wherein Ra, Rb, Rc, Rd' and Rf have the above significance, which is subsequently converted into the corresponding compound of formula I by treatment with a strong base. Suitable bases are, for example, the lower alkali metal alcoholates such as sodium methylate, in which case the corresponding lower alcohol is conveniently used as the solvent. The reaction is preferably carried out at the reflux temperature of the solvent.

The reaction of a compound of formula V in which R' is hydrogen with a compound of formula VI in accordance with process variant b) can be carried out without a solvent or in the presence of a solvent which boils at an elevated temperature. Suitable solvents are, for example, aromatic hydrocarbons such as benzene, toluene and xylene. The cyclocondensation is, however, preferably carried out without a solvent in a temperature range of about 80° C. to about 150° C. The thus-obtained cyclocondensation product, namely a compound of the formula

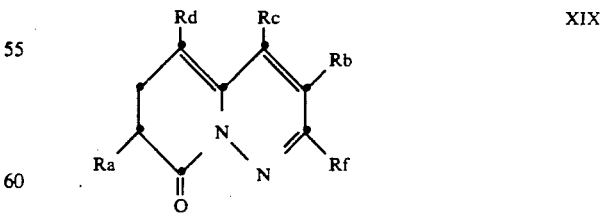

wherein Ra, Rb, Rc, Rd and Rf have the above significance, is subsequently dehydrogenated with a suitable oxidizing agent such as manganese dioxide. Suitable solvents are, for example, aromatic hydrocarbons such as benzene, toluene and xylene. The dehydrogenation is preferably carried out in a temperature range of about room temperature to the boiling temperature of the chosen solvent, preferably at the boiling temperature.

By reacting a compound of formula V in which R' is lower alkoxy in the presence of a strong base such as sodium hydride and in an inert solvent, preferably in an ether such as tetrahydrofuran, with a compound of formula VI in accordance with process variant b), there is obtained the corresponding compound of formula I. The reaction temperature lies in a range of room temperature to the boiling temperature of the reaction mixture.

Compounds of formula I which contain an esterified carboxy group can be hydrolyzed in accordance with process variant c), whereby the corresponding free carboxylic acids are obtained. The hydrolysis can be carried out according to known methods. The hydrolysis is preferably carried out with an alkali metal hydroxide such as sodium hydroxide and potassium hydroxide in a lower alcohol such as methanol and ethanol or in a mixture of a lower alcohol and water. The reaction temperature conveniently lies in a range of room temperature to the boiling temperature of the reaction mixture, preferably at the boiling temperature of the reaction mixture.

Compounds of formula I in which Rd is the group of the formula $-(A^1)_m-CO-O-A^{21}-R^1$ and $A^1$, $A^{21}$, $R^1$ and m have the above significance can be prepared by esterifying a carboxylic acid of formula Ia with an alcohol of formula VII in accordance with process variant d). The esterification can be carried out, for example, in the presence of an esterification reagent in an inert organic solvent. Suitable reagents are, for example, N-methyl-2-chloropyridinium iodide and the like, organic sulfonic acid halides such as methylsulfonyl chloride, p-toluenesulfonyl chloride and mesitylenesulfonyl chloride, and the like. Suitable solvents are, for example, halogenated hydrocarbons such as methylene chloride, chloroform and the like. Suitable bases are, for example, tertiary amines such as triethylamine, tri-n-butylamine and the like. The reaction is preferably carried out in a temperature range of room temperature to the reflux temperature of the solvent.

The desired esterification can also be carried out by firstly converting the carboxylic acid of formula Ia into a reactive derivative and then reacting this with an alcohol of formula VII in the presence of a base. The corresponding carboxylic acid chlorides are preferably used as the reactive derivatives. Suitable bases are, for example, the tertiary amines mentioned previously. The reaction is preferably carried out in a temperature range of about room temperature to the reflux temperature of the reaction mixture, conveniently at room temperature.

The esterification with an alcohol of formula VII in which $A^{21}$ is lower alkylene and $R^1$ is hydrogen, that is, with a lower alcohol, can also be carried out by reacting the carboxylic acid with a N,N-dimethyl-formamide di(lower alkyl)acetal. The reaction with a N,N-dimethyl-formamide di(lower alkyl)acetal is preferably carried out in an inert solvent, for example, in an aromatic hydrocarbon such as benzene, at the reflux temperature of the reaction mixture.

Compounds of formula I in which Rd is the group $-(A^1)_m-CO-NR^2-A^{21}-R^1$ or $-(A^1)_m-CO-NR^3R^4$ and $A^1$, $A^{21}$, $R^1$, $R^2$, $R^3$, $R^4$ and m have the above significance can be prepared by reacting a carboxylic acid of formula Ia or a reactive derivative thereof with an amine of formula IX or X in accordance with process variant e).

By reacting a carboxylic acid of formula VIIIa or a reactive derivative thereof with ammonia of a mono- or di(lower alkyl)amine in accordance with process variant e) there can be prepared corresponding compounds of formula I in which $R^1$ is a group of the formula $-NR^3R^4$ and $R^3$ and $R^4$ together with the nitrogen are a 3- to 7-membered, saturated N-heterocycle which is optionally substituted by one or two lower alkyl groups and which is substituted by a carbamoyl or mono- or di(lower alkyl) carbamoyl group and which can contain as a ring member an oxygen or sulfur atom or the group $>N-R^5$ and $R^5$ has the above significance.

If the free carboxylic acid of formula Ia or VIIIa is used as the starting material, then the amidation reaction is preferably carried out in the presence of a condensation agent such as N-methyl-2-chloropyridinium iodide in an inert organic solvent and in the presence of a base. Suitable solvents are, for example, aromatic hydrocarbons such as benzene, toluene and xylene. Suitable bases are, for example, the tertiary amines mentioned above. Preferred reactive carboxylic acid derivatives which can be reacted in the presence of a base directly with the corresponding amine are the corresponding carboxylic acid chlorides. Suitable bases are again the previously mentioned tertiary amines. Suitable solvents are, for example, aromatic hydrocarbons such as benzene, toluene and xylene and ethers such as dioxane. In both cases the reaction is preferably carried out in a range of room temperature to the reflux temperature of the reaction mixture.

In accordance with process variant f), there can be prepared on the one hand compounds of formula I in which Rd is a group of the formula $-(A^1)_m-O-A^{21}-R^1$ and $A^1$, $A^{21}$, $R^1$ and m have the above significance and on the other hand compounds of formula I which contain a hydroxy group etherified in the form of a lower alkyl ether.

The reaction of a compound of formula Ib' with a compound of formula XI or the reaction of a compound of formula I which contains a free hydroxy group with a compound of formula XII is conveniently carried out in an inert organic solvent such as N,N-dimethylformamide or the like, with a strong base, for example, an alkali metal hydride or hydroxide such as sodium hydride, potassium hydroxide and sodium hydroxide conveniently being used as the base. The reaction is conveniently carried out in a range of 0° C. to room temperature. The leaving group denoted by X is preferably a halogen atom, especially a chlorine, bromine or iodine atom, or an alkylsulfonyloxy or arylsulfonyloxy group, for example a methanesulfonyloxy or p-toluenesulfonyloxy group. In the preparation of lower alkyl ethers X can also are a lower alkoxysulfonyloxy group, that is, the alkylating agent in this case is a di(lower alkyl) sulfate such as dimethyl sulfate.

Compounds of formula I in which Rd is a group of the formula $-(A^1)_m-Q^1-CO-R^1$ and $A^1$, $Q^1$, $R^1$ and m have the above significance can be prepared in accordance with process variant g).

The reaction of a compound of formula Ib with a reactive derivative of a carboxylic acid of formula XIII, for example, a carboxylic acid chloride, is conveniently carried out in an inert organic solvent in the presence of an acid-binding agent, for example, a tertiary amine. Suitable solvent are, for example, aromatic hydrocarbons such as benzene, toluene and xylene and halogenated hydrocarbons such as methylene chloride. When $R^1$ is lower alkyl corresponding carboxylic acid anhydrides can also be used, within this case pyridine conveniently being used as the solvent and as the acid-binding agent. The reaction is preferably carried out in a temperature range of about 0° C. to the boiling temperature of the solvent.

Compounds of formula I in which Rd is a group of the formula $-(A^1)_m-CH_2-NR^2A^{21}-R^1$ or $-(A^1)_m-CH_2-NR^3R^4$ and $A^1$, $A^{21}$, $R^1$, $R^2$, $R^3$, $R^4$ and m have the above significance can be prepared in accordance with process variant h). The reaction is preferably carried out in a lower alcohol as the solvent and with sodium cyanoborohydride as the reducing agent, the reaction being conveniently carried out at room temperature and the amine being conveniently used in the form of its hydrochloride.

Compounds of formula I in which Rd is a group of the formula $-(A^1)_m-R^{12}$ and $R^{12}$ is amino, aminomethyl, hydroxymethyl or methyl and $A^1$ and m have the above significance can be prepared in accordance with process variant i). The choice of the suitable reducing agent depends on the one hand on the starting material which is used and on the other hand on the product which is desired. A compound of formula Id in which $R^{11}$ is cyano can, for example, be reduced with diborane in tetrahydrofuran to the corresponding aminomethyl compound. A compound of formula Id in which $R^{11}$ is nitro can, for example, be reduced with sodium sulfide in a lower alcohol such as methanol to the corresponding amino compound. A compound of formula Id in which $R^{11}$ is lower alkoxycarbonyl can be reduced with lithium borohydride to the corresponding hydroxymethyl compound and the acid chloride of a compound of formula Ia can be reduced with sodium borohydride in tetrahydrofuran and/or dimethylformamide to the corresponding hydroxymethyl compound. A carboxylic acid of formula Ia can, for example, be reduced with borane/tetrahydrofuran complex or borane/methyl sulfide complex in tetrahydrofuran to the corresponding methyl compound.

Compounds of formula I in which Rd is a group of the formula $-(A^1)_m-CHO$ or $-(A^1)_m-(CO)_n-(Q^1A^2)_q-NR^{34}R^{44}$ and $R^{34}$ and $R^{44}$ together are a 3- to 7-membered, saturated N-heterocycle which is optionally substituted by one or two lower alkyl groups and which is substituted by an oxo group and which can contain as a ring member an oxygen or sulfur atom or the group $>N-R^5$, and $A^1$, $A^2$, $Q^1$, $R^5$, m, n and q have the above significance can be prepared in accordance with process variant j). The oxidation of alcohols of formulas Ib' and Ie can be carried out according to methods which are known and which are familiar to any person skilled in the art. For example, the desired oxidation can be carried out with manganese dioxide in a halogenated hydrocarbon such as methylene chloride at room temperature. The desired oxidation can, however, also be carried out with pyridinium chlorochromate in a halogenated hydrocarbon such as methylene chloride at room temperature or with dimethyl sulfoxide/trifluoroacetic acid anhydride in a halogenated hydrocarbon such as methylene chloride at temperatures of about −70° C.

Compounds of formula I in which Rd is a group of the formula $-(A^1)_m-NHCO-R^{13}$, $-(A^1)_m-NH-CO-NR^3R^4$ or $-(A^1)_m-Q^1-CO-NH-R^{33}$ and $R^{13}$ is lower alkoxy, and $A^1$, $Q^1$, $R^3$, $R^{33}$, $R^4$ and m have the above significance can be prepared in accordance with process variant k) by reacting an isocyanate of formula VIIIb with a lower alcohol or an amine of formula X or by reacting an isocyanate of formula XIV with a compound of formula Ib. This reaction is conveniently carried out in an inert solvent, for example, in an aromatic hydrocarbon such as benzene, toluene or xylene, in a halogenated hydrocarbon such as methylene chloride or in an ether such as dioxane. The reaction is preferably carried out in a temperature range of about room temperature to the boiling temperature of the reaction mixture. If an isocyanate of formula XIV in which $R^{33}$ is hydrogen is used as the starting material, then this is conveniently used in protected form. An especially suitable protecting group in this case is the trichloroacetyl group which can be removed by hydrolysis, for example, with potassium carbonate in water, after the reaction has been carried out.

Compounds of formula I in which Rd is a group of the formula $-(A^1)_m-CO-R^{14}$ and $R^{14}$ is lower alkyl, and $A^1$ and m have the above significance can be prepared in accordance with process variant l). Ethers such as tetrahydrofuran are preferably used as the solvent. The reaction is preferably carried out in a temperature range of −78° C. to room temperature.

Compounds of formula I in which Rb and Rc together with the carbon atom denoted as α are a group of the formula $>C_\alpha-S-CH=CH-$ (h) or $>C_\alpha-CH=CH-S-$ (i) which is substituted by halogen can be prepared in accordance with process variant m). Elemental halogen, for example, elemental bromine, is preferably used as the halogenating agent. Suitable solvents are, for example, halogenated hydrocarbons such as chloroform. The halogenation is conveniently carried out in a temperature range of 0° C. to about room temperature.

Compounds of formula I in which Rd is a group of the formula $-(A^1)_m-R^{15}$ and $R^{15}$ is a 5-membered, partially unsaturated or aromatic heterocycle which is attached via a carbon atom and which is optionally substituted by one or two lower alkyl groups and $A^1$ and m have the above significance can be prepared in accordance with process variant n). The reaction of a compound of formula VIIIc with a compound of formula XVI, XVII or XVIII is conveniently carried out in an inert solvent, for example, in a halogenated hydrocarbon such as methylene chloride or in an aromatic hydrocarbon such as benzene, toluene or xylene, and in a temperature range of about 0° C. to the reflux temperature of the reaction mixture. Suitable bases are, for example, the tertiary amines mentioned previously. The cyclization of the thus-obtained product can be carried out according to methods which are known and which are familiar to any person skilled in the art. The cyclization can be carried out, for example, in the presence of catalytic amounts of a strong acid such as p-toluenesulfonic acid while removing the reaction water which is formed by means of a withdrawing agent such as toluene. However, the cyclization can also be carried out by means of diethyl azodicarboxylate/triphenylphosphine in an ether such as tetrahydrofuran.

Compounds of formula I in which Rd is a group of the formula $-(A')_m-CH_2-R^{16}$, A' is $C_{1-6}$—alkyl and $R^{16}$ is lower alkoxycarbonyl and m has the above significance can be prepared in accordance with process variant o). The reaction of a diazoketone of formula VIIId with a lower alcohol is preferably carried out in the presence of a silver catalyst such as silver oxide, the lower alcohol being preferably used as the solvent. The reaction is carried out at an elevated temperature, preferably at the boiling temperature of the reaction mixture.

Compounds of formula I in which Rd is hydrogen can be prepared in accordance with process variant p). The decarboxylation of a carboxylic acid of formula Ia is preferably carried out by dry heating, especially by dry heating in a vacuum to temperatures of about 200° to about 300° C.

Compounds of formula I in which Rd is halogen can be prepared in accordance with process variant q). Suitable halogenating agents for the present halogenation are N-haloimides and N-haloamides such as N-chlorosuccinimide, N-bromosuccinimide, N-chloroacetamide and the like. A halogenated hydrocarbon such as methylene chloride, chloroform, carbon tetrachloride and the like is preferably used as the solvent. The reaction can be carried out in a temperature range of about 0° C. to the boiling temperature of the reaction mixture. The reaction is preferably carried out at room temperature.

Compounds of formula I in which Rd is the group —CHO can be prepared by cleaving the acetal group in a compound of formula VIIIe in accordance with process variant r). The cleavage is preferably carried out by trans-acetalization in the presence of an acid such as p-toluenesulfonic acid and a ketone such as cyclohexanone, acetone and the like. The reaction can be carried out in a temperature range of room temperature to the boiling temperature of the reaction mixture.

Compounds of formula I in which $R^1$ is a group of the formula $—(A^1)_m—OCO—NR^3R^4$ can be prepared in accordance with process variant s). Suitable solvents for the present purpose are, for example, ethers such as tetrahydrofuran, dioxane and diethyl ether, N,N-dimethyl-formamide and dimethyl sulfoxide. The reaction is conveniently carried out at room temperature.

The compounds of formulas II, VIIIa, VIIIb, VIIIc, VIIId, VIIIe and VIIIf which are used as starting materials can be prepared as described hereinafter.

The compounds of formula II can be prepared, for example, by reacting a compound of the formula

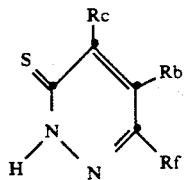

XXI wherein Rb, Rc and Rf have the above significance, with a compound of the formula

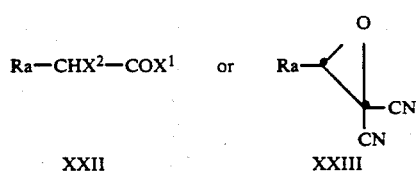

wherein $X^1$ and $X^2$ each are halogen and $R^a$ has the above significance. The reaction of a compound of formula XXI with a compound of formula XXII in which $X^1$ preferably is chlorine and $X^2$ preferably is bromine is preferably carried out at room temperature in a halogenated hydrocarbon such as chloroform, whereupon treatment is carried out with a basic amine such as triethylamine. The reaction of a compound of formula XXI with a compound of formula XXIII is preferably carried out in an inert solvent such as acetone, N,N-dimethylformamide, dimethyl sulfoxide and the like at room temperature.

The carboxylic acids of formula VIIIa can be prepared by hydrolyzing the corresponding lower alkyl esters of formula I. This hydrolysis can be carried out according to methods known, for example, in analogy to process variant c).

The isocyanates of formula VIIIb can be prepared by treating a compound of formula Ib in which $Q^1$ is the group of the formula —NH— in an inert solvent with phosgene. Suitable solvents are, for example, halogenated hydrocarbons such as chloroform and 1,2-dichloroethane. However, the isocyanates of formula VIIIb can also be prepared by converting a carboxylic acid halide of formula VIIIc in an inert organic solvent with an azide such as sodium azide or trimethylsilyl azide into the corresponding carboxylic acid azide and rearranging this to the corresponding isocyanate by heating. Suitable solvents are, for example, ethers such as dioxane, ethylene glycol dimethyl ether, diethylene glycol dimethyl ether and the like, ketones such as ethyl methyl ketone, and the like. The rearrangement is carried out at temperatures of 80° C. and above.

The carboxylic acid halides of formula VIIIc can be prepared by treating a carboxylic acid of formula Ia with a halogenating agent. Suitable halogenating agents are, for example, thionyl chloride, oxalyl chloride, phosphorus pentachloride and the like. In a preferred embodiment excess thionyl chloride is used and the reaction is carried out without an additional solvent at room temperature.

The diazoketones of formula VIIId can be prepared by reacting a carboxylic acid halide of formula VIIIc in an inert organic solvent with diazomethane. Suitable solvents are, for example, ethers such as tetrahydrofuran, dioxane and diethyl ether. The reaction is preferably carried out in a temperature range of about 0° to about 10° C.

The compounds of formula VIIIe can be prepared in analogy to process variant a), there being used as the starting material a compound of the formula HC≡C—CH(OR$^7$)OR$^8$ in which $R^7$ and $R^8$ have the above significance.

The compounds of formula VIIIf can be prepared by reacting a compound of formula Ib' in an inert solvent, for example, in an ether such as dioxane, and in the presence of a base, for example, a basic amine such as pyridine, with phenyl chloroformate.

The remaining compounds which are used as starting materials belong to classes of known substance.

As mentioned earlier, the compounds of formula A have valuable pharmacological properties. In particular, they display pronounced muscle relaxant, sedative-hypnotic, anticonvulsive and/or anxiolytic properties and have only a low toxicity. These properties can be demonstrated, for example, in the antipentetrazole test which is described hereinafter and which is a generally recognized test for establishing such properties.

In this animal experiment, the compound under investigation is administered orally to mice and 30 minutes later there are administered intraperitoneally 120 mg/kg of pentetrazole, which causes emprosthotonus and tonic stretchings of the fore and/or hind limbs in unprotected animals, 1-4 minutes after the injection.

Ten (10) experimental animals are used per dosage of test substance. After counting the protected experimental animals, the $ED_{50}$ is determined according to the known Probit method. The $ED_{50}$ is that dosage which protects 50% of the experimental animals from the spasmodic seizures caused by pentetrazole. The results which have been obtained with representative members of the class of compound defined by formula A in the experiment described previously are compiled in the following Table. Moreover, the Table contains data concerning the acute toxicity ($LD_{50}$) of some of these compounds in mg/kg in the case of single oral administration to mice.

TABLE

| Compound | $ED_{50}$ in mg/kg | $LD_{50}$ in mg/kg p.o. |
| --- | --- | --- |
| A | 3.1 | >3000 |
| B | 0.44 | >3000 |
| C | 0.56 | — |
| D | 0.23 | — |
| E | 1.4 | — |
| F | 3.3 | 3000 |
| G | 8.2 | >5000 |
| H | 0.29 | >5000 |

A = 4-[(10-Chloro-6,7-dihydro-4-oxo-3-phenyl-4H-pyrido-[2,1-a]phthalazin-1-yl)carbonyl]morpholine.
B = (R)-1-[(10-Chloro-6,7-dihydro-4-oxo-3-phenyl-4H-pyrido-[2,1-a]phthalazin-1-yl)carbonyl]-2-(methoxymethyl)-pyrrolidine.
C = 1-[(10-Chloro-6,7-dihydro-4-oxo-3-phenyl-4H-pyrido-[2,1-a]phthalazin-1-yl)carbonyl]-3-methoxyazetidine.
D = 10-Chloro-6,7-dihydro-N,N-dimethyl-4-oxo-3-phenyl-4H-pyrido[2,1-a]phthalazine-1-carboxamide.
E = (R)-1-[(4,5-Dihydro-7-oxo-8-phenyl-7H-pyrido[1,2-b]-thieno[2,3-d]pyridazin-10-yl)carbonyl]-3-methoxy-pyrrolidine.
F = 1-[(4,5-Dihydro-4-methyl-7-oxo-8-phenyl-7H-pyrido-[1,2-b]thieno[2,3-d]pyridazin-10-yl)carbonyl]-3-methoxy-azetidine.
G = 1-[(4,5-Dihydro-5-methyl-7-oxo-8-phenyl-7H-pyrido-[1,2-b]thieno[2,3-d]pyridazin-10-yl)carbonyl]-3-methoxy-azetidine.
H = 4,5-Dihydro-N,N-dimethyl-7-oxo-8-phenyl-7H-pyrido-[1,2-b]thieno[2,3-d]pyridazine-10-carboxamide.

The compounds of formula A and the pharmaceutically acceptable acid addition salts of compounds of formula A which have a basic substituent can be used as medicaments, for example, in the form of pharmaceutical preparations. The pharmaceutical preparations can be administered orally, for example, in the form of tablets, coated tablets, dragees, hard and soft gelatine capsules, solutions, emulsions or suspension. However, the administration can also be carried out rectally, for example, in the form of suppositories, or parenterally, for example, in the form of injection solutions.

For the preparation of pharmaceutical preparations, the products in accordance with the invention can be processed with pharmaceutically inert, inorganic or organic carriers. Lactose, maize starch or derivatives thereof, talc, stearic acid or its salts and the like can be used, for example, as such carriers for tablets, coated tablets, dragees and hard gelatine capsules. Suitable carriers for soft gelatin capsules are, for example, vegetable oils, waxes, fats, semi-solid and liquid polyols and the like. Depending on the nature of the active substance no carriers are, however, generally required in the case of soft gelatin capsules. Suitable carriers for the preparation of solutions and syrups are, for example, water, polyols, saccharose, invert sugar, glucose and the like. Suitable carriers for injection solutions are, for example, water, alcohols, polyols, glycerin, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances. Medicaments containing a product in accordance with the invention and a therapeutically inert carrier as well as a process for their preparation, which comprises bringing a product in accordance with the invention and, if desired, one or more other therapeutically valuable substances into a galenical administration form, are also objects of the present invention.

As mentioned earlier, the products in accordance with the invention can be used in the control or prevention of illnesses, especially in the control of convulsions and anxiety states, as well as for the preparation of medicaments with muscle relaxant, sedative-hypnotic, anticonvulsive and/or anxiolytic properties. The dosage can vary within wide limits and will, of course, be fitted to the individual requirements in each particular case. In the case of oral administration the daily dosage lies in a range of about 1 mg to about 100 mg.

The Examples which follow serve to illustrate further the invention in more detail. All temperatures are given in degrees Celsius, unless otherwise stated.

EXAMPLE I 13.9 g of 7-nitro-1(2H)-phthalazinone and 16.3 g of Lawesson reagent in 170 ml of acetonitrile are heated under reflux for 45 minutes. The reaction mixture is filtered while hot. The filtrate is cooled in an ice-bath and the crystals obtained are removed by filtration under suction. After drying in vacuo and recrystallization there is obtained 7-nitro-1(2H)-phthalazinethione as yellow crystals of m.p. 233°-234° (methanol/acetonitrile).

EXAMPLE II a) 66.95 g of thieno[2,3-d]pyridazine-7(6H)-thione are suspended in 3200 ml of methylene chloride under argon, whereupon 102.7 g of α-bromophenylacetyl chloride are added dropwise thereto. The mixture is stirred at room temperature for about 30 minutes and then 121 ml of triethylamine are added dropwise thereto, whereby the mixture is cooled to 25°-30°. It is stirred for about 40 minutes. After evaporation of the solvent in vacuo, the residue is taken up in 1000 ml of water and 200 ml of ether, whereupon the mixture is stirred for about 30 minutes. The separated crystals are removed by filtration under suction, washed with water and ether and dried overnight. The dried crystals are again triturated with 1000 ml of water. After suction filtration, the red-violet crystals are washed with water and dried in vacuo. There is obtained 3-hydroxy-2-phenyl-thiazolo[3,2-b]thieno [2,3-d]-pyridazin-4-ium hydroxide (internal salt) of m.p. 260°-264° (decomposition).

In an analogous manner, b) from 7-chloro-1(2H)-phthalazinethione and α-bromophenylacetyl chloride, there is obtained, after recrystallization, 9-chloro-3-hydroxy-2-phenyl-thiazolo[2,3-a]phthalazin-4-ium hydroxide (internal salt) of m.p. 296°-298° (chloroform);

c) from 4-methylthieno[2,3-d]pyridazine-7(6H)-thione and α-bromophenylacetyl chloride, there is obtained 7-hydroxy-4-methyl-8-phenylthiazolo[3,2-b]thieno[2,3-d]pyridazin-6-ium hydroxide (internal salt) of m.p. 294°-296° (chloroform).

EXAMPLE III a) 0.41 g of 7-nitro-1(2H)-phthalazinethione and 0.37 g of 3-phenyl-2,2-oxiranedicarbonitrile in 10 ml of acetone are heated under reflux for 30 hours. After cooling in an ice-bath, the violet crystals obtained are removed by filtration under suction, washed with ether and dried in vacuo. There is obtained 9-nitro-3-hydroxy-2-phenyl-thiazolo[2,3-a]-phthalazin-4-ium hydroxide (internal salt) of m.p. 303°-305°.

In an analogous manner, b) from 7-chloro-1(2H)-phthalazinethione and 3-p-chlorophenyl)-2,2-oxiranedicarbonitrile, there is obtained 9-chloro-2-(p-chlorophenyl)-3-hydroxy-thiazolo[2,3-a]phthalazinium hydroxide (internal salt) of m.p. >300° (N,N-dimethylformamide/diethyl ether);

c) from 7-chloro-1(2H)-phthalazinethione and 3-(m-chlorophenyl)-2,2-oxiranedicarbonitrile, there is obtained 9-chloro-2-(m-chlorophenyl)-3-hydroxy-thiazolo[2,3-a]phthalazinium hydroxide (internal salt) of m.p. 298°-300° (N,N-dimethylformamide);

d) from 7-chloro-1(2H)-phthalazinethione and 3-(o-chlorophenyl)-2,2-oxiranedicarbonitrile, there is obtained 9-chloro-2-(o-chlorophenyl)-3-hydroxy-thiazolo[2,3-a]phthalazinium hydroxide (internal salt) of m.p. 289°-291° (N,N-dimethylformamide).

EXAMPLE IV a) 13.5 g of 3-hydroxy-2-phenylthiazolo[3,2-a]phthalazinium hydroxide (internal salt) and 8.1 ml of methyl propiolate are heated under reflux in 200 ml of toluene for 24 hours with the exclusion of moisture. The mixture is then left to cool and is stirred for 1 hour in an ice-bath. The crystals are removed by filtration under suction, dried and finally recrystallized from toluene. There is obtained methyl 4-oxo-3-phenyl-4H-pyrido[2,1-a]phthalazine-1-carboxylate as yellow crystals of m.p. 174°-175°.

In an analogous manner, b) from 3-hydroxy-2-phenylthiazolo[3,2-b]thieno[2,3-d]pyridazin-4-ium hydroxide (internal salt) and methyl propiolate, there is obtained, after recrystallization from acetonitrile, methyl 7-oxo-8-phenyl-7H-pyrido[1,2-b]thieno[2,3-d]pyridazine-10-carboxylate as yellow crystals of m.p. 198°-199°;

c) from 9-chloro-3-hydroxy-2-phenylthiazolo[2,3-a]phthalazin-4-ium hydroxide (internal salt) and methyl propiolate, there is obtained, after recrystallization from acetonitrile, methyl 10-chloro-4-oxo-3-phenyl-4H-pyrido-[2,1-a]phthalazine-1-carboxylate as yellow crystals of m.p. 234°-236°;

d) from 9-nitro-3-hydroxy-2-phenylthiazolo[2,3-a]phthalazin-4-ium hydroxide (internal salt) and methyl propiolate, there is obtained methyl 10-nitro-4-oxo-3-phenyl-4H-pyrido[2,1-a]phthalazine-1-carboxylate of m.p. 227°-230° (N,N-dimethylformamide/methanol);

e) from 9-chloro-2-(p-chlorophenyl)-3-hydroxy-thiazolo-[2,3-a]phthalazinium hydroxide (internal salt) and methyl propiolate, there is obtained methyl 10-chloro-3-(p-chloro-phenyl)-4-oxo-4H-pyrido[2,1-a]phthalazine-1-carboxylate of m.p. 233°-237° (2-propanol/N,N-dimethylformamide);

f) from 7-hydroxy-4-methyl-8-phenylthiazolo[3,2-b]thieno[2,3-d]pyridazin-6-ium hydroxide (internal salt) and methyl propiolate, there is obtained methyl 4-methyl-7-oxo-8-phenyl-7H-pyrido[1,2-b]thieno[2,3-d]pyridazine-10-carboxylate of m.p. 183°-184° (ethyl acetate);

g) from 9-chloro-2-(m-chlorophenyl)-3-hydroxy-thiazolo[2,3-a]phthalazinium hydroxide (internal salt) and methyl propiolate, there is obtained methyl 10-chloro-3-(m-chlorophenyl)-4-oxo-4H-pyrido[2,1-a]phthalazine-1-carboxylate of m.p. 234°-235° (N,N-dimethylformamide/methanol);

h) from 9-chloro-2-(o-chlorophenyl)-3-hydroxy-thiazolo[2,3-a]phthalazinium hydroxide (internal salt) and methyl propiolate, there is obtained methyl 10-chloro-3-(o-chlorophenyl)-4-oxo-4H-pyrido[2,1-a]phthalazine-1-carboxylate of m.p. 220°-222° (acetonitrile).

EXAMPLE V a) 11 g of methyl 4-oxo-3-phenyl-4H-pyrido[2,1-a]phthalazine-1-carboxylate are taken up in 300 ml of ethanol under argon, whereupon a solution of 3.7 g of potassium hydroxide in 30 ml of water is added thereto and the mixture is heated under reflux until the reaction has finished. The reaction mixture is then cooled to room temperature and poured into 2200 ml of water. The mixture is adjusted to pH 7 by adding 1N aqueous hydrochloric acid and impurities are removed by twofold extraction with 300 ml of methylene chloride each time. The aqueous phase is acidified to pH 1 with 2N aqueous hydrochloric acid and the crystals formed are removed by filtration under suction. After repeated washing with water and drying in vacuo, there is obtained 4-oxo-3-phenyl-4H-pyrido[2,1-a]phthalazine-1-carboxylic acid as yellow crystals of m.p. 236°-237° (dec.).

In an analogous manner, b) from methyl 7-oxo-8-phenyl-7H-pyrido[1,2-b]thieno[2,3-d]phthalazine-1-carboxylate, there is obtained, after recrystallization from dimethylformamide, 7-oxo-8-phenyl-7H-pyrido[1,2-b]thieno[2,3-d]pyridazine-10-carboxylic acid as yellow crystals of m.p. 262°-264° (decomposition);

c) from methyl 10-chloro-4-oxo-3-phenyl-4H-pyrido[2,1-a]phthalazine-1-carboxylate, there is obtained, after recrystallization from acetonitrile/dimethylformamide, 10-chloro-4-oxo-3-phenyl-4H-pyrido[2,1-a]phthalazine-1-carboxylic acid as yellow crystals of m.p. 242° (decomposition);

d) from methyl 4-methyl-7-oxo-8-phenyl-7H-pyrido[1,2-b]thieno[2,3-d]pyridazine-10-carboxylate, there is obtained 4-methyl-7-oxo-8-phenyl-7H-pyrido[1,2-b]thieno[2,3-d]pyridazine-10-carboxylic acid of m.p. 243°-245° (acetonitrile/N,N-dimethylformamide).

EXAMPLE VI a) 3.68 g of 4-oxo-3-phenyl-4H-pyrido[2,1-a]phthalazine-1-carboxylic acid are suspended in 80 ml of toluene with the exclusion of moisture, whereupon 5.1 ml of thionyl chloride and 0.2 ml of N,N-dimethylformamide are added thereto and the mixture is stirred at room temperature for 2 hours. The reaction mixture is evaporated in vacuo; the residue is taken up in toluene, whereupon the solution is again evaporated in vacuo. The thus-obtained pure carboxylic acid chloride is taken up in 90 ml of dioxane, whereupon there are added thereto in succession 6.52 ml of triethylamine and 1.4 g of 3-hydroxyazetidine hydrochloride. The mixture is stirred at room temperature until the reaction has finished. After removing the solvent in vacuo, the residue is treated with a mixture of 200 ml of water and 100 ml of saturated aqueous sodium chloride solution, whereupon the mixture is cooled to about 2° and stirred for 30 minutes. The crystals are removed by filtration under suction and washed twice with 15 ml of water. The thus-obtained crystals are dried at 70° in vacuo. The aqueous phase is extracted three times with methylene chloride; the combined organic phases are washed once with 50 ml of water, dried over sodium sulfate, filtered and evaporated. The crystals are combined with the material obtained above and stirred in 150 ml of ether for 30 minutes. The ether is removed by filtration and the yellow crystals are dried. There is obtained 3-hydroxy-1-[(4-oxo-3-phenyl-4H-pyrido[2,1-a]phthalazin-1-yl)carbonyl]azetidine of m.p. 260°–264° (dec.).

In an analogous manner, from 4-oxo-3-phenyl-4H-pyrido[2,1-a]phthalazine-1-carboxylic acid and b) morpholine, there is obtained 4-[(4-oxo-3-phenyl-4H-pyrido[2,1-a]phthalazin-1-yl)carbonyl]morpholine of m.p. 246°–248° (acetonitrile);

c) (R)-2-(methoxymethyl)-pyrrolidine, there is obtained (R)-2-(methoxymethyl)-1-[(4-oxo-3-phenyl-4H-pyrido[2,1-a]phthalazin-1-yl)carbonyl]pyrrolidine of m.p. 187°–189° (ethyl acetate);

d) dimethylamine, there is obtained N,N-dimethyl-4-oxo-3-phenyl-4H-pyrido[2,1-a]phthalazine-1-carboxamide of m.p. 239°–240° (ethanol);

e) (R)-3-methoxy-pyrrolidine, there is obtained (R)-3-methoxy-1-[(4-oxo-3-phenyl-4H-pyrido[2,1-a]phthalazin-1-yl)carbonyl]pyrrolidine of m.p. 208°–209° (ethanol);

f) (S)-3-methoxy-pyrrolidine, there is obtained (S)-3-methoxy-1-[(4-oxo-3-phenyl-4H-pyrido[2,1-a]phthalazin-1-yl)carbonyl]pyrrolidine of m.p. 205°–206° (acetonitrile).

In an analogous manner, from 10-chloro-4-oxo-3-phenyl-4H-pyrido-[2,1-a]phthalazine-1-carboxylic acid and g) N-ethyl-N-(2-methoxyethyl)amine, there is obtained N-ethyl-N-(2-methoxyethyl)-10-chloro-4-oxo-3-phenyl-4H-pyrido[2,1-a]phthalazine-1-carboxamide of m.p. 167° (ethyl acetate);

h) 3-methoxyazetidine, there is obtained 1-[(10-chloro-4-oxo-3-phenyl-4H-pyrido[2,1-a]phthalazin-1-yl)carbonyl]-3-methoxyazetidine of m.p. 238°–240° (acetonitrile);

i) dimethylamine, there is obtained N,N-dimethyl-10-chloro-4-oxo-3-phenyl-4H-pyrido[2,1-a]phthalazine-1-carboxamide of m.p. 244°–246° (ethanol).

j) (R)-3-methoxypyrrolidine, there is obtained (R)-1-[(10-chloro-4-oxo-3-phenyl-4H-pyrido[2,1-a]phthalazin-1-yl)-carbonyl]-3-methoxypyrrolidine of m.p. 204°–206° (acetonitrile);

k) (S)-3-methoxypyrrolidine, there is obtained (S)-1-[(10-chloro-4-oxo-3-phenyl-4H-pyrido[2,1-a]phthalazin-1-yl)carbonyl]-3-methoxypyrrolidine of m.p. 204°–206° (acetonitrile);

l) (S)-prolinol, there is obtained (S)-1-[(10-chloro-4-oxo-3-phenyl-4H-pyrido[2,1-a]phthalazin-1-yl)carbonyl]-2-pyrrolidinemethanol of m.p. 245°–255° (dec.; acetonitrile).

In an analogous manner, from 4-methyl-7-oxo-8-phenyl-7H-pyrido[1,2-b]thieno[2,3-d]pyridazine-10-carboxylic acid and m) dimethylamine, there is obtained N,N,4-trimethyl-7-oxo-8-phenyl-7H-pyrido[1,2-b]thieno[2,3-d]pyridazine-10-carboxamide of m.p. 244°–246° (ethanol);

n) 3-methoxyazetidine, there is obtained 3-methoxy-1-[(4-methyl-7-oxo-8-phenyl-7H-pyrido[1,2-b]thieno[2,3-d]pyridazin-10-yl)carbonyl]azetidine of m.p. 240°–241° (ethanol);

o) (R)-2-(methoxymethyl)-pyrrolidine, there is obtained (R)-2-(methoxymethyl)-1-[(4-methyl-7-oxo-8-phenyl-7H-pyrido[1,2-b]thieno[2,3-d]pyridazin-10-yl)carbonyl]pyrrolidine of m.p. 209°–212° (ethanol);

p) (R)-prolinol, there is obtained (R)-1-[(4-methyl-7-oxo-8-phenyl-7H-pyrido[1,2-b]thieno[2,3-d]pyridazin-10-yl)carbonyl]-2-pyrrolidinemethanol of m.p. 271°–274° (ethanol).

EXAMPLE 1

1.26 g of 1-[(10-chloro-4-oxo-3-phenyl-4H-pyrido[2,1-a]phthalazin-1-yl)carbonyl]-3-methoxyazetidine and 0.75 g of sodium cyanoborohydride in 30 ml of methanol are treated dropwise at room temperature under argon with saturated methanolic hydrochloric acid. The reaction is completed after a short time. The mixture is poured into 70 ml of ice-water and the yellowish crystals are removed by filtration. The crystals are washed three times with 2 ml of water each time and dried at 60° in vacuo. After recrystallization of the crude product from ethyl acetate/acetone (1:1), there is obtained 1-[(10-chloro-6,7-dihydro-4-oxo-3-phenyl-4H-pyrido[2,1-a]phthalazin-1-yl)carbonyl]-3-methoxyazetidine as yellowish crystals of m.p. 238°–239°.

A mixture of tetrahydrofuran and acetic acid can be used in place of methanol as the solvent and in this case no methanolic hydrochloric acid need be added thereto.

In an analogous manner, b) from N-ethyl-10-chloro-N-(2-methoxyethyl-4-oxo-3-phenyl-4H-pyrido[2,1-a]phthalazine-1-carboxamide in methanol/glacial acetic acid (10:1), but without the addition of saturated methanolic hydrochloric acid, there is obtained N-ethyl-10-chloro-6,7-dihydro-N-(2-methoxyethyl)-4-oxo-3-phenyl-4H-pyrido[2,1-a]phthalazine-1-carboxamide of m.p. 184°–185° (ethyl acetate);

c) from 10-chloro-N,N-dimethyl-4-oxo-3-phenyl-4H-pyrido[2,1-a]phthalazine-1-carboxamide in methanol/glacial acetic acid (10:1), but without the addition of saturated methanolic hydrochloric acid, there is obtained 10-chloro-6,7-dihydro-N,N-dimethyl-4-oxo-3-phenyl-4H-pyrido[2,1-a]phthalazine-1-carboxamide of m.p. 250°–252° (ethanol);

d) from 4-[(4-oxo-3-phenyl-4H-pyrido[2,1-a]phthalazine-1-yl)carbonyl]morpholine in methanol/glacial acetic acid (10:1), but without the addition of saturated methanolic hydrochloric acid, there is obtained 4-[(6,7-dihydro-4-oxo-3-phenyl-4H-pyrido[2,1-a]phthalazin-1-yl)carbonyl]morpholine of m.p. 254°–257° (acetonitrile);

e) from methyl 7-oxo-8-phenyl-7H-pyrido[1,2-b]thieno[2,3-d]pyridazine-10-carboxylate in acetic acid there is obtained methyl 4,5-dihydro-7-oxo-8-phenyl-7H-pyrido[1,2-b]thieno[2,3-d]pyridazine-10-carboxylate of m.p. 218° (acetonitrile);

f) from (R)-1-[(10-chloro-4-oxo-3-phenyl-4H-pyrido[2,1-a]phthalazin-1-yl)carbonyl]-2-(methoxymethyl)pyrrolidine, there is obtained (R)-1-[(10-chloro-6,7-dihydro-4-oxo-3-phenyl-4H-pyrido[2,1-a]phthalazin-1-yl)carbonyl]-2-(methoxymethyl)pyrrolidine of m.p. 161°–164° (ethyl acetate/diethyl ether);

g) from 4-[(10-chloro-4-oxo-3-phenyl-4H-pyrido[2,1-a]phthalazin-1-yl)carbonyl]morpholine, there is obtained 4-[(10-chloro-6,7-dihydro-4-oxo-3-phenyl-4H-pyrido[2,1-a]phthalazin-1-yl)carbonyl]morpholine of m.p. 256°–258° (acetonitrile);

h) from (R)-1-[(10-chloro-4-oxo-3-phenyl-4H-pyrido[2,1-a]phthalazin-1-yl)carbonyl]-3-methoxypyrrolidine, there is obtained (R)-1-[(10-chloro-6,7-dihydro-4-oxo-3-phenyl-4H-pyrido[2,1-a]phthalazin-1-yl)carbonyl]-3-methoxypyrrolidine of m.p. 180°–181° (acetonitrile);

i) from (S)-1-[(10-chloro-4-oxo-3-phenyl-4H-pyrido[2,1-a]phthalazin-1-yl)carbonyl]-3-methoxypyrrolidine, there is obtained (S)-1-[(10-chloro-6,7-dihydro-4-oxo-3-phenyl-4H-pyrido[2,1-a]phthalazin-1-yl)carbonyl]-3-methoxypyrrolidine of m.p. 179°–181° (acetonitrile);

j) from (R)-[(7-oxo-8-phenyl-7H-pyrido[1,2-b]thieno[2,3-d]pyridazin-10-yl)carbonyl]-2-pyrrolidinemethanol, there is obtained (R)-1-[(4,5-dihydro-7-oxo-8-phenyl-7H-pyrido[1,2-b]thieno[2,3-d]pyridazin-10-yl)carbonyl]-2-pyrrolidinemethanol of m.p. 218°–219° (methanol);

k) from N-ethyl-N-(2-methoxyethyl)-7-oxo-8-phenyl-7H-pyrido]1,2-b]thieno[2,3-d]pyridazine-10-carboxamide, there is obtained N-ethyl-4,5-dihydro-N-(2-methoxyethyl)-7-oxo-8-phenyl-7H-pyrido[1,2-b]thieno[2,3-d]pyridazine-10-carboxamide of m.p. 148°–149° (ethyl acetate);

l) from N-(3-methoxypropyl)-7-oxo-8-phenyl-7H-pyrido[1,2-b]thieno[2,3-d]pyridazine-10-carboxamide, there is obtained 4,5-dihydro-N-(3-methoxypropyl)-7-oxo-8-phenyl-7H-pyrido[1,2-b]thieno[2,3-d]pyridazine-10-carboxamide of m.p. 220°–221° (acetonitrile);

m) from (R)-3-methoxy-(7-oxo-8-phenyl-7H-pyrido[1,2-b]thieno[2,3-d]pyridazin-10-yl)carbonyl]-pyrrolidine, there is obtained (R)-1-[(4,5-dihydro-7-oxo-8-phenyl-7H-pyrido[1,2-b]thieno[2,3-d]pyridazin-10-yl)carbonyl]-3-methoxypyrrolidine of m.p. 160°–161° (ethyl acetate);

n) from 4-[(7-oxo-8-phenyl-7H-pyrido[1,2-b]thieno[2,3-d]pyridazin-10-yl)carbonyl]morpholine, there is obtained 4-[(4,5-dihydro-7-oxo-8-phenyl-7H-pyrido[1,2-b]thieno[2,3-d]pyridazin-10-yl)carbonyl]-morpholine of m.p. 275°–278° (acetonitrile);

o) from 3-methoxy-1-[(4-methyl-7-oxo-8-phenyl-7H-pyrido[1,2-b]thieno[2,3-d]pyridazin-10-yl)carbonyl]azetidine, there is obtained rac-1-[(4,5-dihydro-4-methyl-7-oxo-8-phenyl-7H-pyrido[1,2-b]thieno[2,3-d]pyridazin-10-yl)carbonyl]-3-methoxyazetidine of m.p. 169°–170° (ethanol);

p) from 3-methoxy-1-[(7-oxo-8-phenyl-7H-pyrido[1,2-b]thieno[2,3-d]pyridazin-10-yl)carbonyl]azetidine, there is obtained 1-[(4,5-dihydro-7-oxo-8-phenyl-7H-pyrido[1,2-b]thieno[2,3-d]pyridazin-10-yl)carbonyl]-3-methoxyazetidine of m.p. 254°–255° (N,N-dimethylformamide/methanol);

q) from N,N-diethyl-7-oxo-8-phenyl-7H-pyrido[1,2-b]thieno[2,3-d]pyridazine-10-carboxamide, there is obtained N,N-diethyl-4,5-dihydro-7-oxo-8-phenyl-7H-pyrido[1,2-b]thieno[2,3-d]pyridazine-10-carboxamide of m.p. 179°–180° (ethyl acetate);

r) from N,N-dimethyl-7-oxo-8-phenyl-7H-pyrido[1,2-b]thieno[2,3-d]pyridazine-10-carboxamide, there is obtained 4,5-dihydro-N,N-dimethyl-7-oxo-8-phenyl-7H-pyrido[1,2-b]thieno[2,3-d]pyridazine-10-carboxamide of m.p. 246°–250° (ethanol/N,N-dimethylformamide);

s) from (S)-2-methoxymethyl-1-[(7-oxo-8-phenyl-7H-pyrido[1,2-b]thieno[2,3-d]pyridazin-10-yl)carbonyl]-pyrrolidine, there is obtained (S)-1-[(4,5-dihydro-7-oxo-8-phenyl-7H-pyrido[1,2-b]thieno[2,3-d]pyridazin-10-yl)carbonyl]-2-(methoxymethyl)pyrrolidine of m.p. 172°–173° (ethanol);

t) from (R)-2-(methoxymethyl)-1-[(7-oxo-8-phenyl-7H-pyrido[1,2-b]thieno[2,3-d]pyridazin-10-yl)carbonyl]pyrrolidine, there is obtained (R)-1-[(4,5-dihydro-7-oxo-8-phenyl-7H-pyrido[1,2-b]thieno[2,3-d]pyridazin-10-yl)carbonyl]-2-(methoxymethyl)pyrrolidine of m.p. 170°–172° (ethanol);

u) from N,N-4-trimethyl-7-oxo-8-phenyl-7H-pyrido[1,2-b]thieno[2,3-d]pyridazine-10-carboxamide, there is obtained 4,5-dihydro-N,N4-trimethyl-7-oxo-8-phenyl-7H-pyrido[1,2-b]thieno[2,3-d]pyridazine-10-carboxamide of m.p. 172°–174° (toluene);

v) from 3-methoxy-1-[(4-oxo-3-phenyl-4H-pyrido[2,1-a]phthalazin-1-yl)carbonyl]azetidine, there is obtained 1-[(6,7-dihydro-4-oxo-3-phenyl-4H-pyrido[2,1-a]phthalazin-1-yl)carbonyl]-3-methoxyazetidine of m.p. 196°–197° (ethanol).

EXAMPLE 2 a) 2.7 g of 10-chloro-N,N-diethyl-4-oxo-3-phenyl-4H-pyrido[2,1-a]phthalazine-1-carboxamide are suspended in 65 ml of tetrahydrofuran under argon, whereupon 150 mg of lithium borohydride are added thereto, the mixture is stirred at room temperature for 4 hours, an additional 75 mg of lithium borohydride are added thereto and the mixture is stirred further until the reaction finishes. The reaction mixture is poured into 300 ml of ice-water, whereby the product crystallizes out. The crude product is chromatographed on silica gel. By recrystallization from toluene, there is obtained 10-chloro-N,N-diethyl-6,7-dihydro-4-oxo-3-phenyl-4H-pyrido[2,1a]phthalazine-1-carboxamide of m.p. 192°–194° (toluene).

In an analogous manner, b) from (S)-1-[(10-chloro-4-oxo-3-phenyl-4H-pyrido[2,1-a]phthalazin-1-yl)carbonyl]-2-(methoxymethyl)pyrrolidine, there is obtained (S)-1-[(10-chloro-6,7-dihydro-4-oxo-3-phenyl-4H-pyrido[2,1-a]phthalazin-1-yl)carbonyl]-2-(methoxymethyl)pyrrolidine of m.p. 166°–167° (ethyl acetate);

c) from (R)-1-[(4-methyl-7-oxo-8-phenyl-7H-pyrido[1,2-b]thieno[2,3-d]pyridazin-10-yl)carbonyl]-2-(methoxymethyl)pyrrolidine, there is obtained (R)-1-[(4,5-dihydro-4-methyl-7-oxo-8-phenyl-7H-pyrido[1,2-b]thieno[2,3-d]pyridazin-10-yl)carbonyl]-2-(methoxymethyl)pyrrolidine of m.p. 150°–155° (toluene/diethyl ether);

d) from (S)-1-[(10-chloro-4-oxo-3-phenyl-4H-pyrido[2,1-a]phthalazin-1-yl)carbonyl]-2-pyrrolidinemethanol, there is obtained (S)-1-[(10-chloro-6,7-dihydro-4-oxo-3-phenyl-4H-pyrido[2,1-a]phthalazin-1-yl)carbonyl]-2-pyrrolidinemethanol of m.p. 222°–225° (methanol/N,N-dimethylformamide);

e) from N,N-dimethyl-4-oxo-3-phenyl-4H-pyrido[2,1-a]phthalazine-1-carboxamide, there is obtained 6,7-dihydro-N,N-dimethyl-4-oxo-3-phenyl-4H-pyrido[2,1-a]phthalazine-1-carboxamide of m.p. 266°–268° (N,N-dimethylformamide/ethanol);

f) from (R)-3-methoxy-1-(4-oxo-3-phenyl-4H-pyrido[2,1-a]phthalazin-1-yl)carbonyl]pyrrolidine, there is obtained (R)-1-[(6,7-dihydro-4-oxo-3-phenyl-4H-pyrido[2,1-a]phthalazin-1-yl)carbonyl]-3-methoxypyrrolidine of m.p. 175°–176° (toluene);

g) from (S)-3-methoxy-1-[(4-oxo-3-phenyl-4H-pyrido[2,1-a]phthalazin-1-yl)carbonyl]pyrrolidine, there is obtained (S)-1-[(6,7-dihydro-4-oxo-3-phenyl-4H-pyrido[2,1-a]phthalazin-1-yl)carbonyl]-3-methoxypyrrolidine of m.p. 174°–175° (toluene);

h) from 10-(3-cyclopropyl-1,2,4-oxadiazol-5-yl)-8-phenyl-7H-pyrido[1,2-b]thieno[2,3-d]pyridazin-7-one, there is obtained 10-(3-cyclopropyl-1,2,4-oxadiazol-5- yl)-4,5-dihydro-7-oxo-8-phenyl-7H-pyrido[1,2-b]thieno[2,3-d]pyridazine of m.p. 202°-204° (toluene);

i) from methyl 10-nitro-4-oxo-3-phenyl-4H-pyrido[2,1-a]phthalazine-1-carboxylate, there is obtained methyl 6,7-dihydro-10-nitro-4-oxo-3-phenyl-4H-pyrido[2,1-a]phthalazine-1-carboxylate of m.p. 232°-233° (N,N-dimethylformamide);

j) from methyl 7-oxo-8-phenyl-7H-pyrido[1,2-b]thieno[2,3-d]pyridazine-10-carboxylate, there is obtained 4,5-dihydro-10-(hydroxymethyl)-8-phenyl-7H-pyrido[1,2-b]thieno[2,3-d]pyridazin-7-one of melting point 205°-206° C. (acetonitrile).

EXAMPLE 3 a) 0.34 g of methyl 7-oxo-8-phenyl-7H-pyrido[1,2-b]thieno[2,3-d]pyridazine-10-carboxylate in 10 ml of formic acid are treated dropwise under argon at 25°-30° with 0.31 g of sodium cyanoborohydride in 2 ml of tetrahydrofuran. The mixture is left to stir at room temperature for 24 hours. The solution is poured into 50 ml of ice-water. The yellowish crystals are removed by filtration and washed with water. After drying in vacuo, recrystallization is carried out from ethyl acetate. There is obtained methyl 4,5-dihydro-5-methyl-7-oxo-8-phenyl-7H-pyrido[1,2-b]thieno[2,3-d]-pyridazine-10-carboxylate of m.p. 180°-181°.

In an analogous manner, b) from 3-methoxy-1-[(7-oxo-8-phenyl-7H-pyrido[1,2-b]thieno[2,3-d]pyridazin-10-yl)carbonyl]azetidine, there is obtained 1-[(4,5-dihydro-5-methyl-7-oxo-8-phenyl-7H-pyrido[1,2-b]thieno[2,3-d]pyridazin-10-yl)carbonyl]-3-methoxyazetidine of m.p. 221°-222° (methanol);

c) from N,N-dimethyl-7-oxo-8-phenyl-7H-pyrido[1,2-b]thieno[2,3-d]pyridazine-10-carboxamide, there is obtained 4,5-dihydro-N,N,5-trimethyl-7-oxo-8-phenyl-7H-pyrido[1,2-b]thieno[2,3-d]pyridazine-10-carboxamide of m.p. 247°-249° (methanol);

d) from (R)-2-(methoxymethyl)-1-(7-oxo-8-phenyl-7H-pyrido[1,2-b]thieno[2,3-d]pyridazin-10-yl)carbonyl]pyrrolidine, there is obtained (R)-1-[(4,5-dihydro-5-methyl-7-oxo-8-phenyl-7H-pyrido[1,2-b]thieno[2,3-d]pyridazin-10-yl)carbonyl]-2-(methoxymethyl)pyrrolidine of m.p. 204°-207° (ethanol);

e) from (S)-1-[(7-oxo-8-phenyl-7H-pyrido[1,2-b]thieno[2,3-d]pyridazin-10-yl)carbonyl]-2-(methoxymethyl)pyrrolidine, there is obtained (S)-1-[(4,5-dihydro-5-methyl-7-oxo-8-phenyl-7H-pyrido[1,2-b]thieno[2,3-d]pyridazin-10-yl)carbonyl]-2-(methoxymethyl)pyrrolidine of m.p. 208°-209° (ethanol);

f) from N,N,4-trimethyl-7-oxo-8-phenyl-7H-pyrido[1,2-b]thieno[2,3-d]pyridazine-10-carboxamide, there is obtained 4,5-dihydro-N,N,4,5-tetramethyl-7-oxo-8-phenyl-7H-pyrido[1,2-b]thieno[2,3-d]pyridazine-10-carboxamide of m.p. 189°-191° (toluene);

g) from (R)-2-(methoxymethyl)-1-[(4-methyl-7-oxo-8-phenyl-7H-pyrido[1,2-b]thieno[2,3-d]pyridazin-10-yl)carbonyl]pyrrolidine, there is obtained (R)-1-[(4,5-dihydro-4,5-dimethyl-7-oxo-8-phenyl-7H-pyrido[1,2-b]thieno[2,3-d]pyridazin-10-yl)carbonyl]-2-(methoxymethyl)pyrrolidine of m.p. 155°-157° (ethyl acetate/diethyl ether);

h) from 3-methoxy-1-[(4-oxo-3-phenyl-4H-pyrido[2,1-a]phthalazin-1-yl)carbonyl]azetidine, there is obtained 1-[(6,7-dihydro-6-methyl-4-oxo-3-phenyl-4H-pyrido[2,1-a]phthalazin-1-yl)carbonyl]-3-methoxyazetidine of m.p. 226°-227° (toluene);

i) from (R)-2-methoxymethyl-1-[(4-oxo-3-phenyl-4H-pyrido[2,1-a]phthalazin-1-yl)carbonyl]pyrrolidine, there is obtained (R)-1-[(6,7-dihydro-6-methyl-4-oxo-3-phenyl-4H-pyrido[2,1-a]pthalazin-1-yl)carbonyl]-2-(methoxymethyl)pyrrolidine of m.p. 158°-159° (ethyl acetate/diethyl ether);

j) from N,N-dimethyl-4-oxo-3-phenyl-4H-pyrido[2,1-a]phthalazine-1-carboxamide, there is obtained 6,7-dihydro-N,N,6-trimethyl-4-oxo-3-phenyl-4H-pyrido[2,1-a]phthalazine-1-carboxamide of m.p. 131°-132° (acetonitrile);

k) from 4-[(10-chloro-4-oxo-3-phenyl-4H-pyrido[2,1-a]phthalazin-1-yl)carbonyl]morpholine, there is obtained 4-[(10-chloro-6,7-dihydro-6-methyl-4-oxo-3-phenyl-4H-pyrido[2,1-a]pyridazin-1-yl)carbonyl]morpholine of m.p. 282°-284° (acetonitrile);

l) from 10-chloro-N,N-diethyl-4-oxo-3-phenyl-4H-pyrido[2,1-a]phthalazine-1-carboxamide, there is obtained 10-chloro-N,N-diethyl-6,7-dihydro-6-methyl-4-oxo-3-phenyl-4H-pyrido[2,1-a]phthalazine-1-carboxamide of m.p. 187°-188° (toluene);

m) from 10-chloro-4-oxo-3-phenyl-N,N-dimethyl-4H-pyrido[2,1-a]phthalazine-1-carboxamide, there is obtained 10-chloro-6,7-dihydro-3-phenyl-N,N,6-trimethyl-4H-pyrido[2,1-a]phthalazine-1-carboxamide of m.p. 231°-233° (acetonitrile).

EXAMPLE 4

0.54 g of methyl 4,5-dihydro-7-oxo-8-phenyl-7H-pyrido[1,2-b]thieno[2,3-d]pyridazine-10-carboxylate are suspended in 16 ml of acetic anhydride and heated to about 100° for 3 hours. The reaction solution is evaporated in vacuo and the residue is taken up in 32 ml of water and stirred up. The mixture is extracted twice with 30 ml of dichloromethane each time and once with 15 ml of dichloromethane. After drying over sodium sulfate, it is filtered and evaporated in vacuo. The residue is chromatographed on silica gel with dichloromethane/acetone (9:1). By recrystallization from ether there is obtained methyl 5-acetyl-4,5-dihydro-7-oxo-8-phenyl-7H-pyrido[1,2-b]thieno[2,3-d]pyridazine-10-carboxylate of m.p. 132°-134°.

EXAMPLE 5

In analogy to Examples V, VI and 2, a) from methyl 10-chloro-3-(p-chlorophenyl)-4-oxo-4H-pyrido[2,1-a]phthalazine-1-carboxylate, there is obtained 4-[(10-chloro-3-(p-chlorophenyl)-6,7-dihydro-4-oxo-4H-pyrido[2,1-a]phthalazin-1-yl)carbonyl]morpholine of m.p. 238°-240° (acetonitrile);

b) from methyl 10-chloro-3-(m-chlorophenyl)-4-oxo-4H-pyrido[2,1-a]phthalazine-1-carboxylate, there is obtained 4-[(10-chloro-3-(m-chlorophenyl)-6,7-dihydro-4-oxo-4H-pyrido[2,1-a]phthalazin-1-yl)carbonyl]morpholine of m.p. 256°-259° (N,N-dimethylformamide/methanol);

c) from methyl 10-chloro-3-(o-chlorophenyl)-4-oxo-4H-pyrido[2,1-a]phthalazine-1-carboxylate, there is obtained 4-[(10-chloro-3-(o-chlorophenyl)-6,7-dihydro-4-oxo-4H-pyrido[2,1-a]phthalazin-1-yl)carbonyl]morpholine of m.p. 200°-202° (ethyl acetate).

EXAMPLE 6 a) 1.26 g of 4-[(10-chloro-6,7-dihydro-4-oxo-3-phenyl-4H-pyrido[2,1-a]phthalazin-1-yl)carbonyl]morpholine are dissolved in 30 ml of dichloromethane under argon, whereupon 1.01 g of tetrabutylammonium hydrogen sulfate, 1.4 g of ethyl iodide and 1.45 ml of 50 percent sodium hydroxide solution are added thereto and the mixture is stirred at room temperature until the reaction has finished. Three (3) ml of water are added thereto. The organic phase is separated and dried, and the solvent is removed in vacuo. The residue is chromatographed on silica gel. After recrystallization there is obtained 4-[(6-ethyl-10-chloro-6,7-dihydro-4-oxo-3-phenyl-4H-pyrido[2,1-a]phthalazin-1-yl)carbonyl]morpholine as yellow crystals of m.p. 288°-289° (acetonitrile).

In an analogous manner, from 4-[(10-chloro-6,7-dihydro-4-oxo-3-phenyl-4H-pyrido[2,1-a]phthalazin-1-yl)carbonyl]morpholine and b) benzyl chloride, there is obtained 4-[(6-benzyl-10-chloro-6,7-dihydro-4-oxo-3-phenyl-4H-pyrido[2,1-a]phthalazin-1-yl)carbonyl]morpholine of m.p. 180°-183° (toluene/diethyl ether).

EXAMPLE 7

2.62 g of 4,5-dihydro-10-(hydroxymethyl)-8-phenyl-7H-pyrido[1,2-b]thieno[2,3-d]pyridazin-7-one are dissolved in 80 ml of N,N-dimethylformamide and cooled to 3° in an ice-bath. 440 mg of 55 percent sodium hydride (NaH) dispersion are added portionwise thereto and the mixture is stirred for an additional hour after the last portion has been added. A solution of 1.5 g of N-chlorocarbonylmorpholine in 3 ml of N,N-dimethylformamide is now added dropwise thereto. The reaction mixture is left to stir at about 5° for an additional 45 minutes and poured into 800 ml of ice-water, whereby the crude product crystallizes out. After washing with water and drying, the crude product is purified by chromatography on silica gel and recrystallization. There is obtained (4,5-dihydro-7-oxo-8-phenyl-7H-pyrido[1,2-b]-thieno[2,3-d]pyridazin-10-yl)methyl-4-morpholinecarboxylate of m.p. 207°-210° (acetonitrile).

EXAMPLE A

Compound A, 4-[(10-chloro-6,7-dihydro-4-oxo-3-phenyl-4H-pyrido[2,1-a]phthalazin-1-yl)carbonyl]morpholine, can be used in a known manner as the active substance for the preparation of pharmaceutical preparations of the following composition:

| (a) Tablets | mg/tablet |
| --- | --- |
| Compound A | 5 |
| Lactose | 135 |
| Maize starch | 51 |
| Polyvinylpyrrolidone | 8 |
| Magnesium stearate | 1 |
| Tablet weight | 200 |

| (b) Capsules | mg/capsule |
| --- | --- |
| Compound A | 10 |
| Lactose | 30 |
| Maize starch | 8.5 |
| Talc | 1 |
| Magnesium stearate | 0.5 |
| Capsule fill weight | 50 |

The compound listed hereinafter can also be used in place of Compound A as the active substance for the preparation of pharmaceutical preparations of the above composition:

Compound B: (R)-1-[(10-chloro-6,7-dihydro-4-oxo-3-phenyl-4H-pyrido[2,1-a]phthalazin-1-yl)carbonyl]-2-(methoxymethyl)pyrrolidine.

I claim:

1. A compound of the formula (A)

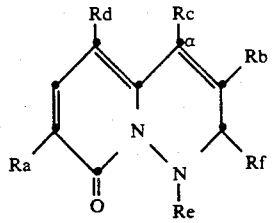

wherein Ra is a phenyl, pyridyl or thienyl group which is unsubstituted or substituted by halogen, trifluoromethyl, nitro, lower alkyl or lower alkoxy, Rb and Rc together with the carbon atom denoted by $\alpha$ are a group of the formula $>C_\alpha$—S—CH=CH (a), or $>C_\alpha$—CH=CH—S— (b) which is unsubstituted or substituted by halogen, trifluoromethyl, lower alkyl, lower alkoxy, nitro, amino or mono- or di(lower alkyl)amino, Rd is the group of the formula —$(A^1)_m$—(CO)-$_n$—$(Q^1A^2)_q$—$R^1$, m, n and q each are the number 0 or 1, $A^1$ is lower alkylene, $A^2$ is lower alkylene, a direct bond or the group —CO—, $Q^1$ is an oxygen atom or the group —$NR^2$—, $R^1$ is hydrogen, hydroxy, cyano, nitro, halogen, lower alkoxy, lower alkyl, lower alkoxycarbonyl, a phenyl group which is unsubstituted or substituted by halogen, trifluoromethyl, lower alkyl, lower alkoxy, nitro, amino or mono- or di(lower alkyl)amino, a group of the formula —$NR^3R^4$ or a 5-membered saturated, partially unsaturated or aromatic heterocycle selected from the group consisting of 2-oxazolinyl, 1,2,4 oxadiazolyl, 2-thiazolyl, and 2-tetrahydrofuryl which is attached via a ring carbon atom and which is unsubstituted or substituted by one or two lower alkyl groups or by a $(C_{3-6})$-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono-or di(lower alkyl) carbamoyl, oxo or alkylenedioxy group, $R^2$ is hydrogen, lower alkyl or a phenyl group which is unsubstituted or substituted by halogen, trifluoromethyl, lower alkyl, lower alkoxy, nitro, amino or mono- or di(lower alkyl)amino, $R^3$ and $R^4$ each, independently, is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$-cycloalkyl group which is unsubstituted or substituted by hydroxy, lower alkoxy, lower alkanoyloxy, lower hydroxyalkyl, lower alkanoyloxy-alkyl, oxo, carbamoyl, mono- or di(lower alkyl)-carbamoyl or by lower alkylenedioxy or $R^3$ and $R^4$ together with the nitrogen atom are a saturated N-heterocycle selected from the group consisting of 1-azetidinyl, 1-pyrrolidinyl, 1-piperidinyl, 4-morpholinyl, 4-thiomorpholinyl, 1-piperazinyl or 4-$R^5$-piperazinyl which is unsubstituted or substituted by one or two lower alkyl groups or by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy groups, $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl) carbamoyl, Re is hydrogen, lower alkyl, lower alkanoyl, phenylcarbonyl, phenyl-(lower alkanoyl), phenyl-(lower alkyl) or lower alkenyl, or a phenylcarbonyl, phenyl- (loweralkanoyl) or phenyl-(lower alkyl) group which is substituted at the phenyl moiety by mono- or di(lower alkyl)amino, and Rf is hydrogen or lower alkyl, with the proviso that n is the number 0 when q is the number 1 and $A^2$ is the group —CO—; that $R^1$ has a significance different from cyano, nitro, halogen or lower alkoxycarbonyl when q is the number 0 and n is the number 1 or when q is the number 1 and $A^2$ is the group —CO—; and, that $R^1$ has a significance different from hydroxy, cyano, nitro, halogen, lower alkoxycarbonyl, lower alkoxy and —$NR^3R^4$ when q is the number 1 and $A^2$ is a direct bond, or a pharmaceutically acceptable acid addition salt of a compound of formula A which has one or more basic substituents.

2. A compound according to claim 1, wherein Rf is hydrogen.

3. A compound according to claim 2, wherein Ra is phenyl.

4. A compound according to claim 3, wherein Rb and Rc together with the carbon atom denoted by α are >$C_α$—S—CH=CH— which is unsubstituted or substituted by halogen.

5. A compound according to claim 4, wherein Rb and Rc together with the carbon atom denoted by α are >$C_α$—S—CH=CH—.

6. A compound according to claim 5, wherein $R^3$ is lower alkyl or lower alkoxyalkyl and $R^4$ is hydrogen or lower alkyl or $R^3$ and $R^4$ together with the nitrogen atom are a 1-azetidinyl, 1-pyrrolidinyl, 1-piperidinyl or 4-morpholinyl which is unsubstituted or substituted by one or two lower alkyl groups or by a hydroxy, lower alkoxy, lower hydroxyalkyl or lower alkoxyalkyl group.

7. A compound according to claim 6, wherein $R^3$ is lower alkyl or 2-(lower alkoxy)ethyl and $R^4$ is hydrogen or lower alkyl or $R^3$ and $R^4$ together with the nitrogen atom are 3-(lower alkoxy)-1-azetidinyl, 3-(lower alkoxy)-1-pyrrolidinyl, 2-(lower alkoxyalkyl)-1-pyrrolidinyl or 4-morpholinyl.

8. A compound according to claim 7, wherein Re is hydrogen or lower alkyl.

9. A compound according to claim 1, (R)-1-[(4,5-Dihydro-7-oxo-8-phenyl-7H-pyrido-[1,2-b]thieno[2,3-d]pyridazin-10-yl)carbonyl]-3-methoxy-pyrrolidine.

10. A compound according to claim 1, 1-[(4,5-Dihydro-4-methyl-7-oxo-8-phenyl-7H-pyrido-[1,2-b]thieno[2,3-d]pyridazin-10-yl)carbonyl]-3-methoxy-azetidine.

11. A compound according to claim 1, 1-[(4,5-Dihydro-5-methyl-7-oxo-8-phenyl-7H-pyrido-[1,2-b]thieno[2,3-d]pyridazin-10-yl)carbonyl]-3-methoxy-azetidine.

12. A compound according to claim 1, 4,5-Dihydro-N,N-dimethyl-7-oxo-8-phenyl-7H-pyrido-[1,2-b]thieno[2,3-d]-pyridazine-10-carboxamide.

13. A pharmaceutical composition comprising an effective amount of a compound of formula (A)

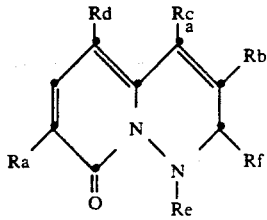

wherein Ra is a phenyl, pyridyl or thienyl group which is unsubstituted or substituted by halogen, trifluoromethyl, nitro, lower alkyl or lower alkoxy, Rb and Rc together with the carbon atom denoted by α are a group of the formula >$C_α$—S—CH=CH— (a), or >$C_α$—CH=CH—S— (b) which is unsubstituted or substituted by halogen, trifluoromethyl, lower alkyl, lower alkoxy, nitro, amino or mono- or di(lower alkyl)amino, Rd is the group of the formula —$(A^1)_m$—(CO)-$_n$—$(Q^1A^2)_q$—$R^1$, m, n and q each are the number 0 or 1, $A^1$ is lower alkylene, $A^2$ is lower alkylene, a direct bond or the group —CO—, $Q^1$ is an oxygen atom or the group —$NR^2$—, $R^1$ is hydrogen, hydroxy, cyano, nitro, halogen, lower alkoxy, lower alkyl, lower alkoxycarbonyl, a phenyl group which is unsubstituted or substituted by halogen, trifluoromethyl, lower alkyl, lower alkoxy, nitro, amino or mono- or di(lower alkyl)amino, a group of the formula —$NR^3R^4$ or a 5-membered saturated, partially unsaturated or aromatic heterocycle selected from the group consisting of 2-oxazolinyl, 1,2,4-oxadiazolyl, 2-thiazolyl and 2-tetrahydrofuryl which is attached via a ring carbon atom and which is unsubstituted or substituted by one or two lower alkyl groups or by a $(C_{3-6})$-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^2$ is hydrogen, lower alkyl or a phenyl group which is unsubstituted or substituted by halogen, trifluoromethyl, lower alkyl, lower alkoxy, nitro, amino or mono- or di(lower alkyl)amino, $R^3$ and $R^4$ each, independently, is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$-cycloalkyl group which is unsubstituted or substituted by hydroxy, lower alkoxy, lower alkanoyloxy, lower hydroxyalkyl, lower alkoxyalkyl, lower alkanoyloxyalkyl, oxo, carbamoyl, mono- or di(lower alkyl)-carbamoyl or by lower alkylenedioxy or $R^3$ and $R^4$ together with the nitrogen atom are a saturated N-heterocycle selected from the group consisting of 1-azetidinyl, 1-pyrrolidinyl, 1-piperidinyl, 4-morpholinyl, 4-thiomorpholinyl, 1-piperazinyl or 4-$R^5$-piperazinyl, which is unsubstituted or substituted by one or two lower alkyl groups or by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy group, $R^5$ is hydrogen, lower alkyl, lower hydroxyalkyl, lower alkoxyalkyl, lower alkanoyloxyalkyl, lower alkanoyl, lower alkoxycarbonyl, carbamoyl, or mono- or di(-lower alkyl)carbamoyl, Re is hydrogen, lower alkyl, lower alkanoyl, phenylcarbonyl, phenyl-(lower alkanoyl), phenyl-(lower alkyl) or lower alkenyl, or a phenylcarbonyl, phenyl-(lower alkanoyl) or phenyl-(lower alkyl) group which is substituted at the phenyl moiety by mono- or di(lower alkyl)amino, and Rf is hydrogen or lower alkyl, with the proviso that n is the number 0 when q is the number 1 and $A^2$ is the group —CO—; that $R^1$ has a significance different from cyano, nitro, halogen or lower alkoxycarbonyl when q is the number 0 and n is the number 1 or when q is the number 1 and $A^2$ is the group —CO—; and, that $R^1$ has a significance different from hydroxy, cyano, nitro, halogen, lower alkoxycarbonyl, lower alkoxy and —$NR^3R^4$ when q is the number 1 and $A^2$ is a direct bond, or a pharmaceutically acceptable acid addition salt of compound of formula A which has one or more basic substituents and a pharmaceutically inert carrier material.

14. A pharmaceutical composition according to claim 13, wherein Rf is hydrogen.

15. A pharmaceutical composition according to claim 14, wherein Ra is phenyl.

16. A pharmaceutical composition according to claim 15, wherein Rb and Rc together with the carbon atom denoted by $\alpha$ are $>C_\alpha-S-CH=CH-$ which is unsubstituted or substituted by halogen.

17. A pharmaceutical composition according to claim 16, wherein Rb and Rc together with the carbon atom denoted by $\alpha$ are $>C_\alpha-S-CH=CH-$.

18. A pharmaceutical composition according to claim 17 wherein $R^3$ is lower alkyl or lower alkoxyalkyl and $R^4$ is hydrogen or lower alkyl or $R^3$ and $R^4$ together with the nitrogen atom are a 1-azetidinyl, 1-pyrrolidinyl, 1-piperidinyl or 4-morpholinyl which is unsubstituted or substituted by one or two lower alkyl groups or by a hydroxy, lower alkoxy, lower hydroxyalkyl or lower alkoxyalkyl group.

19. A pharmaceutical composition according to claim 18, wherein $R^3$ is lower alkyl or 2-(lower alkoxy)ethyl and $R^4$ is hydrogen or lower alkyl or $R^3$ and $R^4$ together with the nitrogen atom are 3-(lower alkoxy)-1-azetidinyl, 3-lower alkoxy)-1-pyrrolidinyl, 2-(lower alkoxyalkyl)-1-pyrrolidinyl or 4-morpholinyl.

20. A pharmaceutical composition according to claim 19, wherein Re is hydrogen or lower alkyl.

21. A method of treating muscle tension, stress, insomnia, anxiety or convulsion in a host requiring such treatment, which comprises administering to said host an effective amount of a compound of the formula (A)

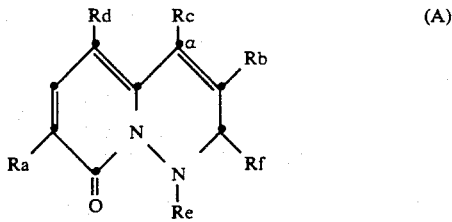

wherein Ra is a phenyl, pyridyl or thienyl group which is unsubstituted or substituted by halogen, trifluoromethyl, nitro, lower alkyl or lower alkoxy, Rb and Rc together with the carbon atom denoted by $\alpha$ are a group of the formula $>C_\alpha-S-CH=CH-$ (a), or $>C_\alpha-CH=CH-S-$ (b) which is unsubstituted or substituted by halogen, trifluoromethyl, lower alkyl, lower alkoxy, nitro, amino or mono- or di(lower alkyl)amino, Rd is the group of the formula $-(A^1)_m-(CO)_n-(Q^1A^2)_q-R^1$, m, n and q each are the number 0 or 1, $A^1$ is lower alkylene, $A^2$ is lower alkylene, a direct bond or the group $-CO-$, $Q^1$ is an oxygen atom or the group $-NR^2-$, $R^1$ is hydrogen, hydroxy, cyano, nitro, halogen, lower alkoxy, lower alkyl, lower alkoxycarbonyl, a phenyl group which is unsubstituted or substituted by halogen, trifluoromethyl, lower alkyl, lower alkoxy, nitro, amino or mono- or di(lower alkyl)amino, a group of the formula $-NR^3R^4$ or a 5-membered saturated, partially unsaturated or aromatic heterocycle selected from the group consisting of 2-oxazolinyl, 1,2,4-oxadiazolyl, 2-thiazolyl and 2-tetrahydrofuryl which is attached via a ring carbon atom and which is unsubstituted or substituted by one or two lower alkyl groups or by a $(C_{3-6})$-cycloalkyl, hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or alkylenedioxy group, $R^2$ is hydrogen, lower alkyl or a phenyl group which is unsubstituted or substituted by halogen, trifluoromethyl, lower alkyl, lower alkoxy, nitro, amino or mono- or di(lower alkyl)amino, $R^3$ and $R^4$ each, independently, is hydrogen, lower alkyl, lower alkoxyalkyl, lower dialkoxyalkyl, lower alkylenedioxyalkyl, lower cyanoalkyl, lower haloalkyl, lower hydroxyalkyl, lower dihydroxyalkyl, lower alkanoyl, lower alkoxycarbonyl or a $(C_{3-7})$-cycloalkyl group which is unsubstituted or substituted by hydroxy, lower alkoxy, lower alkanoyloxy, lower hydroxyalkyl, lower alkoxyalkyl, lower alkanoyloxy-alkyl, oxo, carbamoyl, mono- or di(lower alkyl)carbamoyl or by lower alkylenedioxy or $R^3$ and $R^4$ together with the nitrogen atom are a saturated N-heterocycle selected from the group consisting of 1-azetidinyl, 1-pyrrolidinyl, 1-piperidinyl, 4-morpholinyl, 4-thiomorpholinyl, 1-piperazinyl or $4-R^5$-piperazinyl, which is unsubstituted or substituted by one or two lower alkyl groups or by one or two hydroxy, lower alkoxy, lower alkanoyloxy, lower hydroxyalkyl, lower alkoxyalkyl, lower alkanoyloxyalkyl, lower alkoxycarbonyl, lower alkanoyl, carbamoyl, mono- or di(lower alkyl)carbamoyl, oxo or lower alkylenedioxy group, $R^5$ is hydrogen, lower alkyl, lower hydroxyalkyl, lower alkoxyalkyl, lower alkanoyloxyalkyl, lower alkanoyl, lower alkoxycarbonyl, carbamoyl or mono- or di(lower alkyl)carbamoyl, Re is hydrogen, lower alkyl, lower alkanoyl, phenylcarbonyl, phenyl-(lower alkanoyl), phenyl-(lower alkyl) or lower alkenyl, or a phenylcarbonyl, phenyl-(lower alkanoyl) or phenyl-(lower alkyl) group which is substituted at the phenyl moiety by mono- or di(lower alkyl)amino, and Rf is hydrogen or lower alkyl, with the proviso that n is the number 0 when q is the number 1 and $A^2$ is the group $-CO-$; that $R^1$ has a significance different from cyano, nitro, halogen or lower alkoxycarbonyl when q is the number 0 and n is the number 1 or when q is the number 1 and $A^2$ is the group $-CO-$; and, that $R^1$ has a significance different from hydroxy, cyano, nitro, halogen, lower alkoxycarbonyl, lower alkoxy and $-NR^3R^4$ when q is the number 1 and $A^2$ is a direct bond, or a pharmaceutically acceptable acid addition salt of compound of formula A which has one or more basic substituents.

22. A method according to claim 21, wherein Rf is hydrogen.

23. A method according to claim 22, wherein Ra is phenyl.

24. A method according to claim 23, wherein Rb and Rc together with the carbon atom denoted by $\alpha$ are $>C_\alpha-S-CH=CH-$ which is unsubstituted or substituted by halogen.

25. A method according to claim 24, wherein Rb and Rc together with the carbon atom denoted by $\alpha$ are $>C_\alpha-S-CH=CH-$.

26. A method according to claim 25, wherein $R^3$ is lower alkyl or lower alkoxyalkyl and $R^4$ is hydrogen or lower alkyl or $R^3$ and $R^4$ together with the nitrogen atom are a 1-azetidinyl, 1-pyrrolidinyl, 1-piperidinyl or 4-morpholinyl which is unsubstituted or substituted by one or two lower alkyl groups or by a hydroxy, lower alkoxy, lower hydroxyalkyl or lower alkoxyalkyl group.

27. A method according to claim 26, wherein $R^3$ is lower alkyl or 2-(lower alkoxy)ethyl and $R^4$ is hydrogen or lower alkyl or $R^3$ and $R^4$ together with the nitrogen atom are 3-(lower alkoxy)-1-azetidinyl, 3-(lower alkoxy)-1-pyrrolidinyl, 2-(lower alkoxyalkyl)-1-pyrrolidinyl or 4-morpholinyl.

28. A method according to claim 27, wherein Re is hydrogen or lower alkyl.

* * * * *